(12) United States Patent
Adahan

(10) Patent No.: US 8,317,774 B2
(45) Date of Patent: *Nov. 27, 2012

(54) SUCTION SYSTEM

(76) Inventor: Carmeli Adahan, Jerusalem (IL)

( * ) Notice: Subject to any disclaimer, the term of this patent is extended or adjusted under 35 U.S.C. 154(b) by 411 days.

This patent is subject to a terminal disclaimer.

(21) Appl. No.: 12/451,335

(22) PCT Filed: May 6, 2008

(86) PCT No.: PCT/IL2008/000624
§ 371 (c)(1),
(2), (4) Date: Nov. 6, 2009

(87) PCT Pub. No.: WO2008/135997
PCT Pub. Date: Nov. 13, 2008

(65) Prior Publication Data
US 2010/0063483 A1    Mar. 11, 2010

Related U.S. Application Data

(60) Provisional application No. 60/924,268, filed on May 7, 2007.

(51) Int. Cl.
*A61M 27/00* (2006.01)
*A61M 1/00* (2006.01)
(52) U.S. Cl. .......... 604/543; 604/313; 604/315
(58) Field of Classification Search .......... 604/313–316, 604/540, 543
See application file for complete search history.

(56) References Cited

U.S. PATENT DOCUMENTS

| | | | |
|---|---|---|---|
| 1,599,899 A | | 9/1926 | Kettering et al. |
| 2,954,738 A | * | 10/1960 | Di Vette .................. 417/383 |
| 2,999,500 A | * | 9/1961 | Schurer .................. 604/322 |
| 3,416,461 A | | 12/1968 | McFarland |
| 3,680,560 A | * | 8/1972 | Pannier et al. ............ 604/320 |
| 3,780,738 A | * | 12/1973 | Deaton .................. 604/540 |
| 4,306,557 A | * | 12/1981 | North .................... 604/119 |
| 4,321,922 A | * | 3/1982 | Deaton .................. 604/319 |
| 4,447,226 A | | 5/1984 | Mayoral |
| 4,611,627 A | | 9/1986 | Eidsvoog et al. |
| 4,642,088 A | * | 2/1987 | Gunter .................. 604/6.15 |
| 4,661,093 A | | 4/1987 | Beck et al. |
| 4,739,791 A | | 4/1988 | Adahan |
| 4,930,997 A | | 6/1990 | Bennett |

(Continued)

FOREIGN PATENT DOCUMENTS

DE    24 01 643 A1    7/1975
(Continued)

OTHER PUBLICATIONS

Extended European Search Report, six pages, for corresponding European Application No. 10163456.6, mailed on Apr. 26, 2012.

*Primary Examiner* — Susan Su
(74) *Attorney, Agent, or Firm* — Vorys, Sater, Seymour and Pease LLP; Susanne M. Hopkins; William L. Klima

(57) ABSTRACT

A system and method are disclosed for providing suction to a target area, in which suction is induced via pumping action in proximity to the target area via a pump head that is integral with an enclosure that is configured for covering the area. The pump head has an inlet that projects directly into the internal volume of the enclosure.

21 Claims, 5 Drawing Sheets

U.S. PATENT DOCUMENTS

| | | | |
|---|---|---|---|
| 5,295,982 A * | 3/1994 | Schatz | 604/313 |
| 5,370,610 A | 12/1994 | Reynolds | |
| 5,419,687 A | 5/1995 | Adahan | |
| 5,549,584 A | 8/1996 | Gross | |
| 5,636,643 A | 6/1997 | Argenta et al. | |
| 5,645,081 A | 7/1997 | Argenta et al. | |
| 5,662,599 A | 9/1997 | Reich et al. | |
| 5,735,833 A * | 4/1998 | Olson | 604/289 |
| 5,776,119 A | 7/1998 | Bilbo et al. | |
| 6,042,560 A | 3/2000 | Niederberger | |
| 6,071,267 A | 6/2000 | Zamierowski | |
| 6,471,982 B1 | 10/2002 | Lydon et al. | |
| 6,520,931 B2 * | 2/2003 | Suh | 604/73 |
| 6,562,013 B1 | 5/2003 | Marasco, Jr. | |
| 6,648,862 B2 | 11/2003 | Watson | |
| 6,824,533 B2 | 11/2004 | Risk, Jr. et al. | |
| 6,899,693 B2 | 5/2005 | Ghelli et al. | |
| 7,128,735 B2 | 10/2006 | Weston | |
| 7,273,465 B2 | 9/2007 | Ash | |
| 7,503,910 B2 * | 3/2009 | Adahan | 604/319 |
| 7,532,953 B2 * | 5/2009 | Vogel | 700/282 |
| 7,981,098 B2 * | 7/2011 | Boehringer et al. | 604/313 |
| 8,057,449 B2 * | 11/2011 | Sanders et al. | 604/319 |
| 8,080,702 B2 * | 12/2011 | Blott et al. | 602/41 |
| 8,105,295 B2 * | 1/2012 | Blott et al. | 604/315 |
| 2001/0029956 A1 | 10/2001 | Argenta et al. | |
| 2003/0014022 A1 | 1/2003 | Lockwood et al. | |
| 2003/0040687 A1 | 2/2003 | Boynton et al. | |
| 2003/0050594 A1 | 3/2003 | Zamierowski | |
| 2003/0097100 A1 | 5/2003 | Watson | |
| 2004/0028756 A1 | 2/2004 | Teather et al. | |
| 2004/0039243 A1 | 2/2004 | Bearnson et al. | |
| 2004/0039330 A1 | 2/2004 | Silver | |
| 2004/0059284 A1 | 3/2004 | Nash et al. | |
| 2004/0064132 A1 | 4/2004 | Boehringer et al. | |
| 2005/0004534 A1 * | 1/2005 | Lockwood et al. | 604/304 |
| 2005/0065471 A1 | 3/2005 | Kuntz | |
| 2005/0070859 A1 | 3/2005 | Cull et al. | |
| 2005/0192548 A1 | 9/2005 | Dolliver et al. | |
| 2007/0010798 A1 * | 1/2007 | Stoller et al. | 604/544 |
| 2007/0055209 A1 * | 3/2007 | Patel et al. | 604/315 |
| 2007/0167926 A1 * | 7/2007 | Blott et al. | 604/304 |
| 2008/0108977 A1 * | 5/2008 | Heaton et al. | 604/543 |
| 2009/0005746 A1 * | 1/2009 | Nielsen et al. | 604/315 |
| 2009/0012483 A1 * | 1/2009 | Blott et al. | 604/315 |
| 2010/0298793 A1 * | 11/2010 | Blott et al. | 604/319 |
| 2011/0028918 A1 * | 2/2011 | Hartwell | 604/319 |
| 2011/0054421 A1 * | 3/2011 | Hartwell | 604/319 |
| 2011/0087179 A2 * | 4/2011 | Blott et al. | 604/319 |

FOREIGN PATENT DOCUMENTS

| | | |
|---|---|---|
| DE | 102 15 896 A1 | 10/2003 |
| DE | 20 2005 019 670 U1 | 6/2006 |
| EP | 0 156 211 A2 | 10/1985 |
| EP | 0 865 304 B1 | 9/1998 |
| EP | 1 163 915 A2 | 12/2001 |
| GB | 2 307 180 A | 5/1997 |
| GB | 2 378 734 A | 2/2003 |
| WO | 96/05873 A1 | 2/1996 |
| WO | 97/18007 A1 | 5/1997 |
| WO | 99/44650 A1 | 9/1999 |
| WO | 00/02016 A1 | 1/2000 |
| WO | 03/016719 A1 | 2/2003 |
| WO | 03/030966 A1 | 4/2003 |
| WO | 03/057070 A2 | 7/2003 |
| WO | 2004/037334 A1 | 5/2004 |
| WO | 2005/051461 A1 | 6/2005 |
| WO | 2006052745 A2 | 5/2006 |
| WO | 2007/013049 A1 | 2/2007 |
| WO | 2007/013064 A1 | 2/2007 |
| WO | 2007013064 A1 | 2/2007 |
| WO | 2007030601 A2 | 3/2007 |

* cited by examiner

SUCTION SYSTEM

This is a National Phase Application filed under 35 U.S.C. 371 as a national stage of PCT/IL2008/000624, filed May 6, 2008, an application claiming the benefit under 35 U.S.C. 119(e) U.S. Provisional Application No. 60/924,268, filed May 7, 2007, the content of each of which is hereby incorporated by reference in its entirety.

FIELD OF THE INVENTION

This invention relates to suctioning systems and methods, and particularly to such systems and methods that apply negative pressure to physiological areas and the like.

BACKGROUND OF THE INVENTION

Applying negative pressure to a physiological area such as a wound, for example, enhances drainage of fluids or exudate from the wound and promotes tissue growth and wound healing. This method of healing (known as "cupping") was exercised since the times of ancient Greek physicians until the 19th century. Applying negative pressure to other physiological areas such as burn, for example, is also beneficial even when there is no draining.

There are also other situations in which it may be desired to apply a vacuum or suctioning to a particular volume, such as to prevent or minimize contamination of the pump drive unit, for example when removing flowable contaminated, toxic or hazardous materials from a particular location.

By way of general background, a number of systems and methods have been developed for providing suctioning and/or for treatment of wounds, for example as disclosed in the following publications, which also include a number of examples of pumps and venting valves, the contents of which are incorporated herein in their entirety: WO96/05873, WO 97/18007, WO 03/016719 (US 2004/028756, GB 2,378,734), U.S. Pat. No. 6,648,862; U.S. Pat. No. 5,645,081; GB 2,307, 180 (EP 0865304); U.S. Pat. No. 4,739,791; WO 03/030966; US2004/0064132; WO 2006/052745; WO 03/057070; US 2005/192548; WO 2007/013049; WO 2007/013064, U.S. Pat. No. 5,370,610, U.S. Pat. No. 5,662,599, U.S. Pat. No. 6,471,982, U.S. Pat. No. 5,636,643, U.S. Pat. No. 7,128,735, U.S. Pat. No. 6,824,533, U.S. Pat. No. 6,562,013, U.S. Pat. No. 4,447,226, U.S. Pat. No. 4,611,627, U.S. Pat. No. 1,599, 899, WO 00/02016, EP 156211, DE 2401643, U.S. Pat. No. 6,071,267, US 2005/004534, US 2004/039243, US 2003/014022, U.S. Pat. No. 3,416,461, U.S. Pat. No. 5,419,687, US 2001/029956, US 2001/029956, DE 10215896, U.S. Pat. No. 6,042,560, U.S. Pat. No. 4,930,997, U.S. Pat. No. 4,661,093, U.S. Pat. No. 5,776,119, US 2004/059284, US 2003/097100, US 2003/040687, US 2003/050594, WO 2004/037334.

SUMMARY OF THE INVENTION

Herein, the term "target", "target area", or "target volume" interchangeably relate to any body, system or environment to which it is desired to apply a negative or sub-ambient pressure to and/or to drain fluids therefrom.

Herein, the term "medical target volume" relates to target, target area, or target volume comprising any part (external or internal) of the body of a human or animal, regarding which it is desired to apply a negative or sub-ambient pressure to and/or to drain fluids therefrom. By way of non-limiting example, such a target volume may comprise a wound or a burn, for example on an external body surface, e.g. the skin.

The term "fluid" as used herein includes liquids and/or gases, including air, and may optionally include solids mixed in with said liquids and/or gases.

According to a first aspect of the invention, there is provided a system for providing suction to and optionally suctioning fluids from a target area, comprising:

a suction head assembly comprising an enclosure having an open end, said enclosure adapted to be in fluid communication with at least a portion of said target area via said open end (i.e., said enclosure being adapted for covering said target area such that the target area is enclosed in the enclosure and in fluid communication therewith) and a pump head comprising a pumping chamber having an inlet and an outlet, wherein said pump head is integrated with said enclosure, and wherein said inlet is comprised in said enclosure and is in fluid communication therewith;

wherein said system is adapted for selectively providing a predetermined working pressure within said enclosure below ambient pressure of an external environment via operation of said pump head.

Suction within the enclosure is induced via the inlet, which is also used for suctioning fluids therethrough from the target area. For example, the target area may be a medical target volume associated with a wound, burn or the like, and said enclosure is configured for being sealable to a perimeter of the wound, burn or the like, respectively, on an external body part, e.g. skin, so as to define a confined volume within the enclosure.

In illustrated embodiments, the pump head and said enclosure may be integrally joined with or mounted to one another.

The system comprises a powered drive apparatus comprising a drive unit coupled to a primary pump, in operation said powered drive apparatus being configured for operating said pump head via a non-mechanical coupling arrangement when driven by said drive unit. In particular, the pump head may comprise an actuation chamber that is mechanically coupled to said pumping chamber, and wherein said non-mechanical coupling arrangement comprises a pneumatic coupling arrangement comprising a control volume of working fluid that pneumatically couples said primary pump with said actuating chamber, said mechanical coupling being configured for enabling said drive unit to operate said pump head by inducing pumping of said pumping chamber via pneumatic coupling between said primary pump and said actuation chamber. Such mechanical coupling comprises a pump member included in said pump head and defining part of said pumping chamber and part of said actuation chamber, wherein said pump member is actuable via said pneumatic coupling to generate said working pressure, and wherein said pump member constitutes a fluid barrier member substantially preventing fluid communication between said enclosure and said pump drive. The pump head may comprise a casing, and pump member may be in the form of a diaphragm having first and second opposite facing surfaces and sealingly mounted at a periphery thereof to an inside of said casing to divide said inside of said casing, respectively defining said pump chamber, comprising said first surface, and said actuating chamber, comprising said second surface, and wherein said pump member is configured for offering no substantial resistance to deformation and/or movement under the action of a pressure differential across said first and second surfaces.

Optionally, the enclosure comprises at least one of a flange made from a compliant material and sealable over a body part comprising said target area and a screen provided at said open end. Further optionally, the screen may be integral with the flange and/or the enclosure.

The said suction pump assembly is remotely releasably connected to said powered drive apparatus via said non-mechanical coupling arrangement. Such a coupling may include a length of tubing pneumatically connecting the pump head to the primary pump.

In disclosed embodiments, the primary pump comprises a primary pump member, for example a piston or diaphragm adapted for forced reciprocation within a primary pump casing and said pump drive comprises a rotary motor, and wherein said powered drive apparatus comprises a reciprocation arrangement for converting rotary motion of said motor to reciprocative motion of said primary pump member, said primary pump member being in fluid communication with said actuation chamber via said control volume during operation of said system. In at least some embodiments, the pump member comprises a piston member, and wherein said pump member and said piston member are pneumatically coupled one with the other via said control volume at least when said system is in operation. In other embodiments, a diaphragm arrangement is used instead of the piston.

The system may in any case further comprise a waste container defining a collection volume for collection of materials that may be drained from said target area via said suction head assembly during operation of said system, wherein said waste container is in fluid communication with an outlet port of said pumping chamber.

Optionally, and in at least some embodiments, at least one of said suction pump assembly and said waste container is configured for being disposable.

A non fluid invasive monitoring system may be provided for said system, with respect to fluids to be sucked via said pump head, for monitoring said working pressure, said monitoring system comprising at least one pressure sensor in fluid communication with said control volume and configured for monitoring a pressure thereof.

A control system may also be provided for controlling operation of the said system, Optionally, the system may further comprise a suitable structure that it may be desired to have in contact or in fluid communication with said target area, such that fluid communication between the target and the pump head is via said structure. For example, said structure may comprise at least one of a porous and/or medicated dressing, a filter, a matrix of suitable material, porous foam, gauze, bandage, and the like.

According to at least a first embodiment of the invention and at least some variations thereof, the system further comprises one or more of the following features in any combination:

(A) A venting arrangement adapted for providing, at least during operation of said system, substantially permanent fluid communication between said enclosure and said external environment, such as to enable said working pressure to be maintained at the target area while enabling a desired flow rate of ambient air into the enclosure to be provided via said venting arrangement. The venting arrangement may comprise at least one bleeding orifice comprising an effective flow area compatible with providing said desired flow rate. The venting arrangement also serves as a means for equalizing the enclosure pressure with ambient pressure when the primary pump is not operating.

(B) A controllable venting arrangement adapted for regulating, at least during operation of said system, the vacuum level at said target area. For example, the controllable venting arrangement may comprise any one of a pressure regulator and a solenoid valve.

(C) A controllable venting arrangement adapted for controlling, at least during operation of said system, the vacuum level at said control volume. For example, the controllable venting arrangement comprises any one of a pressure regulator and a solenoid valve.

(D) A port adapted for connection to an irrigation source for providing, at least during operation of said system, fluid communication between said enclosure and said irrigation source, such as to enable irrigation of said target area with a desired irrigation material.

(E) The primary pump may comprise bleeding means for allowing controlled fluid communication between said control volume and an outside environment, said bleeding means being of predetermined size to allow for the relative synchronization between the primary pump member and actuation chamber (F) The primary pump comprises a bleeding means, for example a gap, between said primary pump member and said primary pump casing for allowing controlled fluid communication between said control volume and an outside environment, as in (E), said gap being of predetermined size such as to limit said fluid communication and enable operation of the system to provide a level of said working pressure ranging from a relatively low level of below-ambient pressure when the primary pump member is reciprocated at a relatively slow rate, and a relatively high level of below-ambient pressure when the primary pump member is reciprocated at a relatively fast rate.

According to at least a second embodiment of the invention and at least some variations thereof, the system further comprises one or more of the following features in any combination:

(a) The actuation chamber is configured for displacing a first maximum volume of working fluid within said control volume between maximum and minimum extremes of actuation of said pump member respectively corresponding to a maximum positive pressure and a maximum suction pressure induced at said pumping chamber, and wherein said primary pump is configured for displacing a second maximum volume of working fluid within said control volume as said primary pump element undergoes a reciprocation cycle, wherein said second maximum volume is greater than said first maximum volume.

(b) The pump drive comprises a stepper motor. Further optionally, the stepper motor further may comprise a flywheel configured for rotating with said motor. The system may be configured for operating said motor to selectively turn in any direction for any desired angular displacement and to selectively reverse direction. For example, the system may be configured for operating said motor to be alternately turned in clockwise and counterclockwise directions through respective positive and negative angular displacement of predetermined size to provide a corresponding reciprocation of said primary pump element and generating a respectively alternating positive pressure and suction pressure at said pumping chamber to thereby generate said working pressure at said enclosure in operation of the system, wherein levels of said positive pressure and suction pressure are a function of said angular displacement up to a first maximum angular displacement corresponding to said maximum and minimum extremes of actuation of said pump member respectively, wherein in operation of said system, said enclosure is sealingly affixed over said target area.\

(c) A first venting arrangement adapted for providing, at least during operation of said system, selective fluid communication between said enclosure and said external environment, such as to enable said target area to be selectively vented to ambient pressure via said first venting arrangement. The first venting arrangement comprises, for example, a passageway between said enclosure and an outside environment and having a venting valve which is biased in its datum configuration to close fluid communication via said passageway, said venting valve being configured to be openable responsive to a predetermined force acting thereon, wherein said system is configured for selectively providing said force via said pump element, under conditions wherein said primary pump member provides a pressure stroke beyond that required for actuating said pump member to provide said maximum positive pressure at said pump chamber.

(d) A controllable second venting arrangement adapted for selectively regulating the pressure level of said control volume. The controllable venting arrangement may be configured for synchronizing said system by controlling the fluid pressure in said control volume prior to operative use of said system. For example, the controllable venting arrangement may comprise a controllable solenoid valve.

According to the first aspect of the invention there is also provided a suction head assembly for use with the system according to the first aspect of the invention, the suction head assembly, which may be provided as a kit, comprises:

an enclosure having an open end adapted to be in fluid communication with at least a portion of said target area via said open end, and a pump head comprising a pumping chamber having an inlet and an outlet, wherein said pump head is integrated with said enclosure, and wherein said inlet is comprised in said enclosure and is in fluid communication therewith;

said suction head assembly configured for operating within the system when coupled thereto to selectively provide a predetermined working pressure within said enclosure below ambient pressure of an external environment via operation of said pump head.

In illustrated embodiments, the pump head and said enclosure may be integrally joined with or mounted to one another.

The pump head may be configured for being operated by a powered drive apparatus comprising a drive unit coupled to a primary pump, in operation said powered drive apparatus being configured for operating said pump head via a non-mechanical coupling arrangement when driven by said drive unit. In particular, the pump head may comprise an actuation chamber that is mechanically coupled to said pumping chamber, and wherein said non-mechanical coupling arrangement comprises a pneumatic coupling arrangement comprising a control volume of working fluid that pneumatically couples said primary pump with said actuating chamber, said mechanical coupling being configured for enabling said drive unit to operate said pump head by inducing pumping of said pumping chamber via pneumatic coupling between said primary pump and said actuation chamber. Such mechanical coupling comprises a pump member included in said pump head and defining part of said pumping chamber and part of said actuation chamber, wherein said pump member is actuable via said pneumatic coupling to generate said working pressure, and wherein said pump member constitutes a fluid barrier member substantially preventing fluid communication between said enclosure and said pump drive. The pump head may comprise a casing, and pump member may be in the form of a diaphragm having first and second opposite facing surfaces and sealingly mounted at a periphery thereof to an inside of said casing to divide said inside of said casing, respectively defining said pump chamber, comprising said first surface, and said actuating chamber, comprising said second surface, and wherein said pump member is configured for offering no substantial resistance to deformation and/or movement under the action of a pressure differential across said first and second surfaces.

Optionally, the enclosure comprises at least one of a flange made from a compliant material and sealable over a body part comprising said target area and a screen provided at said open end. Further optionally, the screen may be integral with the flange and/or the enclosure.

The said suction pump assembly is configured for being remotely releasably connected to said powered drive apparatus via said non-mechanical coupling arrangement. Such a coupling may include a length of tubing pneumatically connecting the pump head to the primary pump.

The pump assembly may further comprise a waste container coupled thereto, the waste container defining a collection volume for collection of materials that may be drained from said target area via said suction head assembly during operation of said system, wherein said waste container is in fluid communication with an outlet port of said pumping chamber.

Optionally, and in at least some embodiments, at least one of said suction pump assembly and said waste container is configured for being disposable.

Optionally, the pump assembly may further comprise a suitable structure that it may be desired to have in contact or in fluid communication with said target area, such that fluid communication between the target and the pump head is via said structure. For example, said structure may comprise at least one of a porous and/or medicated dressing, a filter, a matrix of suitable material, porous foam, gauze, bandage, and the like.

According to at least a first embodiment of the invention and at least some variations thereof, the pump assembly further comprises one or more of the following features (A) to (D) disclosed above, mutatis mutandis, in any combination:

According to at least a second embodiment of the invention and at least some variations thereof, the system further comprises a first venting arrangement adapted for providing, at least during operation of said system, selective fluid communication between said enclosure and said external environment, such as to enable said target area to be selectively vented to ambient pressure via said first venting arrangement. The first venting arrangement comprises, for example, a passageway between said enclosure and an outside environment and having a venting valve which is biased in its datum configuration to close fluid communication via said passageway, said venting valve being configured to be openable responsive to a predetermined force acting thereon, wherein said system is configured for selectively providing said force via said pump element, under conditions wherein said primary pump member provides a pressure stroke beyond that required for actuating said pump member to provide said maximum positive pressure at said pump chamber.

According to the first aspect of the invention, there is also provided a method for providing suction to and optionally suctioning fluids from a target area, comprising:

providing a suitable enclosure having an open end for covering said target area such that said enclosure is in fluid communication with at least a portion of said target area via said open end, providing a predetermined working pressure within said enclosure below ambient pressure of an external environment;

wherein said working pressure is generated by a working pressure source in close proximity to said enclosure and is directly applied thereto.

A feature of at least some embodiments of the invention, is that while fluids may be drawn into the pumping chamber of the pump head by suction, they are forced to the waste container by a positive gauge pressure force.

Another feature of at least some embodiments of the invention is that the pressure used for pumping fluids or exudates from the pump chamber may be high, without affecting the sub-ambient pressure generated at the target area.

Yet another feature of at least some embodiments of the invention is that the pump head is isolated from the primary pump, and there is no fluid communication between the pumping chamber of the pump unit and the primary pump itself preventing fluid that may be within the pumping chamber from contaminating the primary pump or other parts of the powered drive apparatus, for example the transducer.

Yet another feature of at least some embodiments of the invention is the use of a single conduit to provide coupling between the primary pump and the actuation chamber, and which may further be used for monitoring the vacuum level at the target area.

The working fluid is typically air, but may instead comprises any suitable gas. Alternatively, the working fluid may be a non-compressible fluid, for example water or other liquid, and the control volume hydraulically couples the primary pump chamber with the actuation chamber.

Thus, according to the first aspect of the invention, a system and method are disclosed for providing suction to a target area, in which suction is induced via pumping action in proximity to the target area via a pump head that is integral with an enclosure that is configured for covering the area. The pump head has an inlet that projects directly into the internal volume of the enclosure.

According to a second aspect of the invention, there is provided a pump apparatus comprising a pump head comprising a pumping chamber having an inlet and an outlet, and further comprising a powered pump drive including a stepper motor arrangement, in operation said stepper motor arrangement being configured for driving said pump head and thus enabling said pump head to induce a suction via the pump inlet.

For example, the pump head comprises a pump member defining part of said pumping chamber, said pump member being reciprocably actuable when operated by said pump drive, said pump drive comprising a reciprocating mechanism for converting rotational motion provided by said stepper motor to reciprocating motion for driving said pump head. The pump member may be a diaphragm or piston, for example.

For example, the pump member may be directly actuable by the pump drive via the reciprocating mechanism, which is mechanically coupled to the pump member, for example via, mutatis mutandis, the mechanical coupling disclosed in WO 03/016719 and WO 2007/013064, by the present applicant, the contents of which are incorporated herein in their entirety.

In another example, the pump member may be indirectly actuable by the pump drive and the reciprocating mechanism, via non-mechanical coupling, e.g., pneumatic coupling, for example as disclosed for the first aspect of the invention, mutatis mutandis.

In some applications, the pump apparatus according to the second aspect of the invention is configured for applying a suction to a target area, and optionally for suctioning fluids therefrom, and further comprises an enclosure having an opening for covering and enclosing the target area. Suction is provided to the enclosure by the pump head directly, for example according to the first aspect of the invention, or via a length of conduit or the like providing fluid communication between the enclosure and the pump head, for example as disclosed in WO 2007/013064, mutatis mutandis.

In any case, the stepper motor may further comprise a flywheel configured for rotating with said motor.

The system may be configured for operating said motor to selectively turn in any direction for any desired angular displacement and to selectively reverse direction to thereby control pumping action of said pump head.

In one mode of operation, the motor may be controlled by a suitable control system to slow its rotational speed at angular positions corresponding to the opening of one or another of the valves that are respectively included in the pump head inlet and outlet, and the speed may raised after the respective valve is fully open. A feature of this arrangement is noise reduction in operation of the system.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
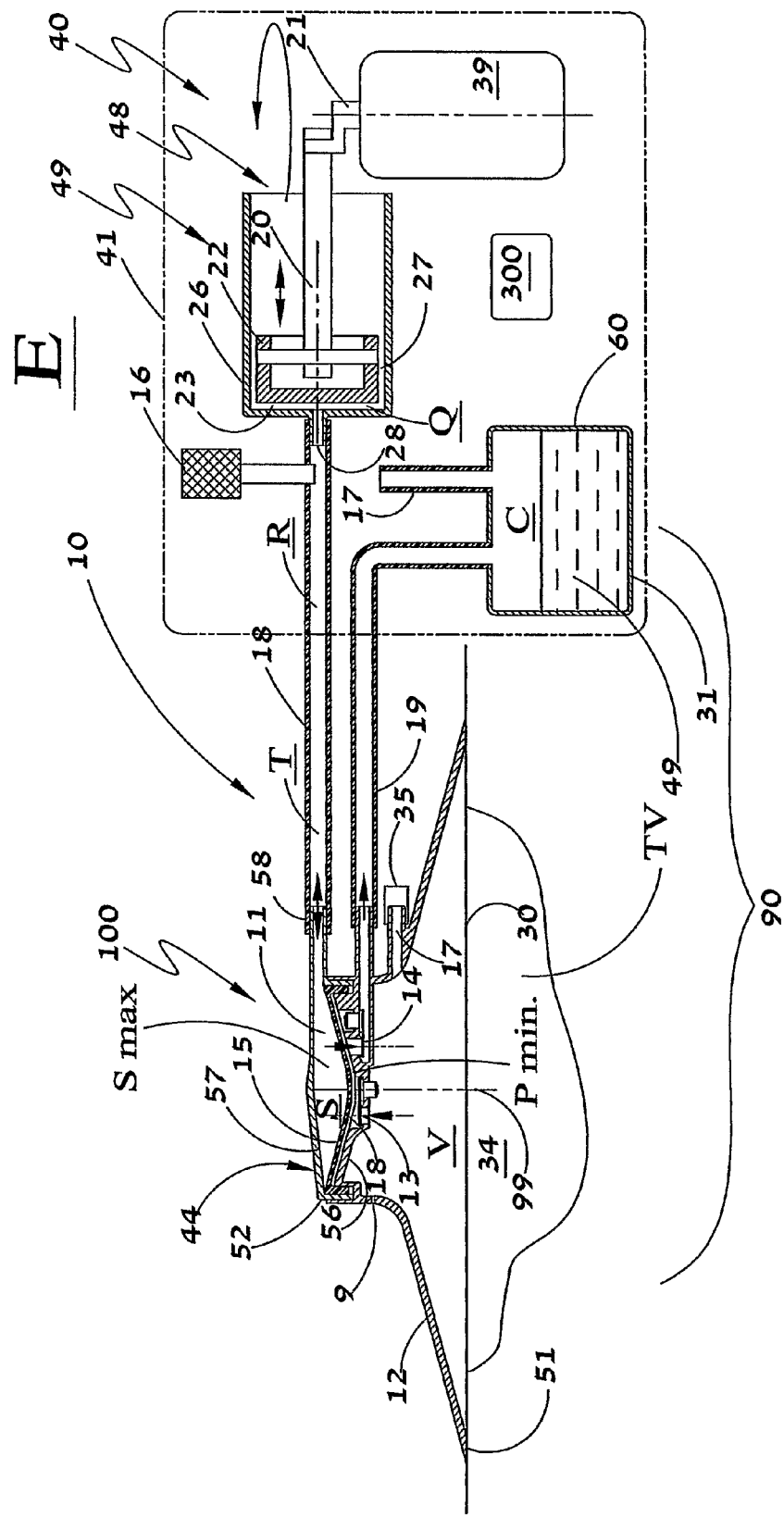
FIG. 1 is a schematic illustration in cross-sectional side view of a first embodiment of the invention, with the slave pump head in the pressure stroke.

A vacuum system for providing, i.e. applying, a negative pressure or sub-ambient pressure to a target area TV, in particular a medical target volume, and thus for enabling fluids to be drained therefrom, according to a first embodiment of the present invention, illustrated in FIG. 1 and generally designated with the numeral 10, comprises a suction head assembly 100, waste container 31, and powered drive apparatus 40.

Figure 2:
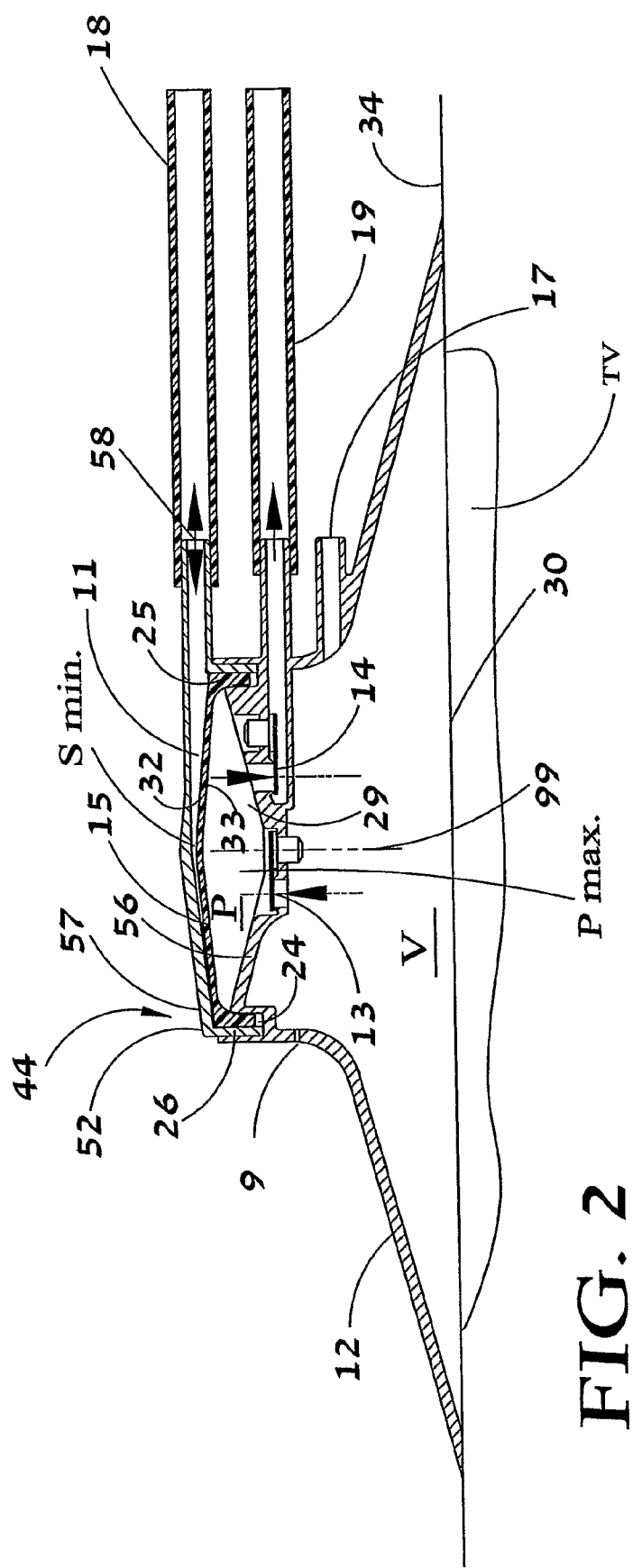
FIG. 2 shows in greater detail the suction head assembly of the embodiment of FIG. 1, with the slave pump head in the suction stroke.

Referring also to FIG. 2, the suction head assembly 100 comprises an enclosure and a slave pump head 44. The enclosure may be in the form of wound enclosure 12, which is associated with the target area or medical target volume comprising a body wound, for example, and has an open end 30 adapted for covering a target volume to be in fluid communication therewith. The enclosure 12 has an outer perimeter 51 that is sealable to the periphery of the wound area on the body 34. In operation, the enclosure 12 defines a confined volume V covering and including the target volume TV over the exposed parts of the wound from which it is desired to remove under suction fluids, for example liquids and other flowable materials, which may include biological and/or non-biological materials, though alternatively it may be desired merely to maintain a negative pressure in the confined volume V over the wound to promote healing thereof, for example.

The slave pump head 44 is in the form of a dual chambered diaphragm type pump head, and comprises a substantially rigid or semi rigid casing 52, i.e., sufficiently rigid to enable operation of the pump head 44 during pressure and suction modes, as will become clearer below, comprising a first part 56 and a second part 57. A barrier member 15 essentially divides the internal volume of the casing 52 into a pumping chamber 29, defined between the first part 56 and barrier member 15, and a juxtaposed actuation chamber 11, defined between the barrier member 15 and the second part 57. The barrier member 15 is sealingly connected at its periphery to the wall of casing 52, and comprises a pump chamber facing surface 33 and an actuation chamber facing surface 32. The first part 56 comprises a pump inlet port 13 and a pump outlet port 14, and suitable one-way valves are provided at the pump inlet port 13 and a pump outlet port 14 to ensure fluid flow in one direction through the pump head 44 from inlet port 13 to outlet port 14 via pumping chamber 29. Inlet port 13 essentially constitutes the outlet of the enclosure 12 for exudates and fluids pumped from the target volume TV.

The barrier member 15 is substantially impervious to the fluids being transported through the pump head 44 during operation thereof, and acts as a pumping member, and the pumping chamber 29 provides a variable pumping volume P, the barrier member 15 being reversibly actuable, in this embodiment and variations thereof deformable and/or movable, between a first, full positive pressure position in contact or close proximity to the rigid part 56 to define a minimum pump volume $P_{min}$ (illustrated in FIG. 1), and a second, full suction position (when maximally spaced from the rigid part 56 during operation of the system) to define a maximum pump volume $P_{max}$ (illustrated in FIG. 2). At the same time, the actuation chamber 11 comprises a variable volume S that varies in inverse relationship with respect to pumping volume P, so that as S reaches a maximum value $S_{max}$, P reaches $P_{min}$, and vice versa.

Barrier member 15 is configured for responding to changes in pressure between the pump chamber facing surface 33 and the actuation chamber facing surface 32 thereof such as to equalize the pressures acting on the surfaces 32 and 33 of the barrier member 15. For example, the barrier member 15 may be in the form of a diaphragm (also referred to herein as a membrane), in particular a highly flexible diaphragm or a rolling diaphragm, which merely floats back and forth with the movement of media present on both sides, offering no substantial resistance to deformation and/or movement under the action of a pressure differential across its surfaces 32 and 33 in a manner such as to correspondingly change the volumes S and P in a mutually substantially complementary manner. Thus, under the action of a positive pressure differential between surfaces 32 and 33, the barrier member 15 is deformed and/or moved towards the first part 56 to assume a generally concave configuration, while under the action of a negative pressure differential, the barrier member 15 is deflected outwardly to assume a substantially convex configuration.

Thus, barrier member 15 provides two functions, isolating the pumping chamber 29 from the actuation chamber 11, such as to prevent any fluid communication or contamination therebetween, and of equalizing the pressures acting on either surfaces 32 and 33 of the barrier member 15, i.e., between the two chambers 11, 29, by changing the relative magnitudes of the volumes thereof. Thus, the barrier member 15 may comprise any suitable material and/or structure that enables the two functions to be performed, and in this and at least some variations of this embodiment may be configured as a fluid impermeable membrane capable of translating, moving or otherwise deforming with respect to the first part 56 and second part 57, thereby correspondingly changing the magnitude of the volumes P and S.

According to an aspect of the invention, and referring again to the first embodiment of the invention, the enclosure 12 is integrated with a slave pump head 44. By "integrated" is meant that the enclosure is mechanically coupled to the pump head 44 to form an integrated unit or unitary device, whether integrally joined or mounted with respect to one another, such that the inlet port 13 is comprised in, projects into, or is in close proximity to, the inside of the enclosure 12, i.e. volume V, at least with respect to the length of the fluid connection between the outlet port 14 and the drive unit 40, for example. In other words, in terms of fluid communication, volume P is significantly closer to volume V via inlet port 13, than volume S is to the drive unit 40, the pump head 44 being remote from the drive unit 40.

Thus, for example, the enclosure 12 and pump head 44 are mutually mounted or otherwise joined with respect to one another—for example the enclosure 12 may be mounted or integrally joined to the pump head 44 or vice versa. In particular, the first part 56 may be integrally formed with the enclosure 12, forming a peripheral groove 24, into which is received an annular mounting ring 25 formed integrally with the barrier member 15 at the periphery thereof. The second part 57 may also comprise a ring 26 which is also received in the grove 24 and provides a sealing fit for the ring 25, and thus the barrier member 15, with respect to the first part 56 and second part 57.

In the illustrated embodiment, the volume V of enclosure 12 is substantially free, providing direct fluid communication between the target volume TV and the pump head 44, without the need for, and in the absence of, any connecting conduits between the enclosure 12 and the inlet 13. Alternatively, and in alternative variations of the first embodiment, the inlet 13 may be formed such that it is outside the enclosure 12 or not in direct fluid communication therewith when open, and a short passageway or length of conduit, for example not generally greater than a characterizing dimension of the assembly 100, provides indirect fluid communication between the volume V and the inlet 13. In such alternative embodiments the short passageway or length of conduit are considered herein as being part of the inlet 13.

In the illustrated embodiment in FIGS. 1 and 2, the volume V provides unhindered passage of fluids to the pump head 44 from the target. Optionally, though, the volume V may comprise any suitable structure that it may be desired to have in contact or in fluid communication with the target, so that fluid communication between the target area TV and the pump head 44 is via this interface accommodated in volume V. Such an interface may comprise, for example, a porous and/or medicated dressing, a filter, a matrix of suitable material, porous foamed pad, gauze, and so on, and there are many examples in the art of such interfaces used in combination with a wound enclosure.

A conduit 19 provides fluid communication between the pump volume P and the container 31 via outlet port 14, which is formed having a port axis generally orthogonal to the valve axis 99, though in alternative variations of this embodiment, the port axis for outlet port 14 may be inclined at any suitable angle to axis 99.

The waste container 31 comprises a suitable housing 60 defining a collection volume C adapted for collecting waste materials, particularly liquids and other flowable materials, from the wound or other target volume to which the system is coupled. Thus, the housing 60 is substantially at least one of impermeable, contamination and leak-free regarding these materials with respect to the external environment, and may be formed as an integral item, or from several parts suitably joined together, for example. The container 31 may be rigid or semi rigid, though in alternative variations of the embodiment, the container may be flexible and/or collapsible. In variations of this embodiment where the container is flexible and/or collapsible, the waste container may be made from thin plastic sheet or any other suitable flexible or non-rigid material, for example, which allow it to be folded or collapsed when not full, providing the convenience of having minimal bulk and minimal inconvenience to the user/patient using or carrying it.

In the illustrated embodiment, the container 31 also comprises a vent 17 for venting the collection volume C to the external environment. A suitable biological filter, hydrophobic filter or other filter (not shown) may optionally be provided at vent 17 to prevent contamination of the external environment from the contents of the container 31. Alternatively or additionally, and depending on the particular application of vacuum system 10, a suitable filter, valve or barrier may be provided for preventing ingress of contaminants from the external environment to volume C. In alternative variations of this embodiment, the container may be provided as a collapsed bag, and thus there is no displacement of existing fluid from inside the container as it fills with exudates and fluids, pumped thereto from the pump assembly.

Optionally, the waste container 31 may contain a porous media, absorbent material, or the like, adapted to soak up or effectively increase the viscosity of or otherwise trap drained liquids received from enclosure 12.

The powered pump, apparatus 40 comprises drive unit 39 and primary pump 49. The drive unit 39 is accommodated in housing 41, and comprises a powered drive, such as an electric motor, and optionally a battery pack (not shown) for powering the motor. Additionally or alternatively, the motor or drive unit 39 may be provided with power from an external source, such as for example an electric mains (not shown). Optionally, the speed of the motor may be variable, for example the motor 39 may be a stepper motor.

The system 10 may further comprise a system 300 for controlling at least one operative parameter of the motor 39.

A reciprocating mechanism 48, comprising a crank 21 coupled to a reciprocating rod 20, is provided within the housing 41 for converting the rotary drive of the motor 39 to reciprocating motion of rod 20. Alternatively, in other variations of the first embodiment of the invention, the powered drive of the powered pump apparatus 40 may comprise a linear motor, mutatis mutandis, for example comprising a suitable solenoid, coaxially or otherwise suitably connected to the rod 20 for providing reciprocating motion thereto, as the direction of travel of the linear motor is alternately reversed, and optionally, the speed of the linear motor may be controllably varied.

The drive unit 39 is coupled to primary pump 49, which in this embodiment is in the form of a piston pump, comprising a piston 22 reciprocable within a cylinder 26 to provide a master pump chamber 23 having a variable pumping volume Q. The reciprocating rod 20 is connected to the piston 22 and is driven in a two-way forced reciprocation manner by means of the rod when the system 10 is in operation to periodically vary the magnitude of volume Q between a maximum and minimum value.

The second part 57 comprises a port 58 that provides fluid communication between the actuation chamber 11 and the powered pump apparatus 40, in particular the master pump chamber 23, via a conduit 18 or the like having internal volume R.

The pumping volume Q, volume S and the internal volume R together define a control volume T of working fluid that couples the piston 22 with the barrier member 15. Typically, the working fluid is air, and thus the control volume T pneumatically couples the master pump chamber 23 with the actuation chamber 11.

Thus, as the motor 39 operates and drives reciprocation of the piston 22, a corresponding pulsating flow is set up in the control volume T, alternately increasing and decreasing the volume of the actuation chamber 11, which in turn respectively decreases and increases the volume P of slave pump chamber 29, providing a periodic suction force in the enclosure 12. Thus, fluids in the enclosure 12 may be periodically sucked directly into pump chamber 29 via inlet 13, and then out of the pump chamber 29, under pressure, to the container 31 via outlet 14 and conduit 19.

In operation, as the motor 39 turns continuously in one direction, the piston 22 is reciprocated in alternate opposed directions towards and away from the opposed end of the inside of chamber 23, cyclic pressure is applied to the control volume T of air in chamber 23, which in turn pneumatically causes a corresponding displacement and/or deformation of the barrier member 15, which in turn causes the volume of pump chamber 29 to contract and expand, thereby enabling fluids to be pumped from the enclosure 12 to the container 31 via conduit 19. The pressure within the chamber 23 thus fluctuates in a cyclic manner, and the peak suction pressure in the chamber 23, which generally coincides with the maximum travel of the piston in one direction, corresponds to and is nominally equal to the maximum suction level at the pump chamber 29, since the barrier member 15 deforms/translates to equalize pressure across it.

A controlled leakage outlet, in the form of a radial clearance or gap 27 of predetermined size provided between the piston 22 and cylinder 26, allows fluid communication between the master pump chamber 23 and an outside of the chamber 23, for example the outside environment E. As the piston 22 reciprocates in cylinder 26, there will be leakage of the working fluid, in this example air, into and out of the chamber 23, as the piston maximizes and minimizes, respectively, volume Q. The size of the gap 27 is relatively small with respect to the volume Q, and is chosen such that relative magnitude of the leaked air volume, per reciprocation cycle, with respect to the nominal control volume T, will vary according to the reciprocation speed of the piston, and thus the rotational speed of the motor 39. The slower the motor operates, the larger the leak volume, and conversely the faster the motor operates, the lower the leak volume. Thus, when it is desired to have a relatively larger suction force at the enclosure 12, the motor speed may be increased, and vice versa when a relatively lower suction force is needed, regarding the suction stroke of the piston, i.e., in suction mode, when the piston is moved in the direction to maximize volume Q. Similarly, when it is desired to have a relatively larger pressure force at the enclosure 12, the motor speed may be increased, and vice versa when a relatively lower pressure force is needed, regarding the pressure stroke of the piston, i.e., in pressure mode, when the piston is moved in the direction to minimize volume Q. According to aspects of the invention, the speed of the piston 22, during suction mode, may be the same or different from the speed of the piston 22 during pressure mode. For example, it may be desired to generate a modest vacuum at the enclosure 12, but also to provide a strong driving pressure to drive exudates in the chamber 29 under positive pressure towards the container 31—in such a case, the speed of the piston during the pressure mode may be substantially higher than during the suction mode in any one reciprocation cycle.

The gap 27 ensures in a natural manner that the connecting the pump head 44 is synchronized with the primary pump 49, after these are interconnected via conduit 18 and prior to using the system 10 (or at the start whenever using the system as well), to ensure that the full suction position of the barrier member 15 corresponds to the full suction position of the piston 22. For example, when the volume S of the actuation chamber is at $S_{max}$, the piston 23 can slowly move to the position corresponding to $Q_{min}$, synchronizing the position of piston 23 with barrier member 15 as working fluid is controllably leaked out of control volume T.

In alternative variations of this embodiment the control volume T may be substantially air tight, and thus there is no gap 27. In such variations of the first embodiment the pump head 44 is synchronized with the primary pump 49, prior to using the system 10, in a different manner, for example by manually setting the barrier member 15 to its full suction position, corresponding to $S_{min}$ and the piston 22 to its full suction position, corresponding to $Q_{max}$ and interconnecting the pump head 44 with the primary pump 49 via conduit 18 while not disturbing the respective positions of the barrier member 15 or the piston 22.

In alternative variations of this embodiment, the piston 22 may be sealingly reciprocable within the cylinder, and the leakage outlet may be instead formed as an aperture of appropriate size in the cylinder or piston that allows controlled leakage from the chamber 23.

Alternatively, and in yet other variations of the first embodiment of the invention, the piston pump arrangement for the primary pump 49 may be replaced with a diaphragm type pump arrangement, for example, in which the pump volume Q is instead defined by a chamber formed between a diaphragm and a casing of the pump arrangement, the diaphragm being coupled to the motor to reciprocate as the motor turns. A controlled leak may be provided to the control volume T by providing one or more holes in the diaphragm that enable fluid communication between this pump chamber and an outside thereof. Operation of this arrangement is otherwise identical to that of the piston pump arrangement described above, mutatis mutandis. In further alternative variations of this embodiment the diaphragm type pump may be fully sealed.

The control volume T is in fluid communication with at least one pressure sensor or transducer 16, or alternatively with any other suitable air pressure measuring device, for monitoring the pressure therein. For example, the transducer 16 may have a conduit spliced into conduit 18, and is furthermore operatively connected to control system 300. The control system 300 may thus be adapted for monitoring and optionally controlling at least one operative parameter of the motor 39. The transducer 16 provides feedback signals or data—for example electrical, electronic or digital—thereto representative of the absolute or gauge pressure in the actuation chamber 11, and thus of the pressure in pump chamber 29.

In operation of the system, the suction pressure at the pump chamber 29 is nominally equal to that at the wound enclosure 12, since the two are juxtaposed and in close proximity in terms of fluid communication, via port 13. The absence of a conduit, or at least of a relatively long length of conduit interposed to connect the pump chamber 29 and the wound enclosure 12 facilitates equalization of the suction pressures between the pump chamber 29 and the wound enclosure 12 during operation of the system 10. Thus, the peak suction pressure at the chamber 23 nominally closely corresponds to the peak suction pressure provided at the wound enclosure 12, and thus monitoring of the chamber pressure via transducer 16 generally provides a measure of the pressure at the enclosure 12; at the same time, the transducer 16 is effectively isolated from the pump chamber 29 via the barrier member 15. In alternative variations of the first embodiment, the transducer 16 and its connection to the system may be omitted.

In the illustrated embodiment, the said waste container 31 is accommodated in housing 41, and may be selectively removed therefrom for disposal, for example, optionally while still connected to the suction head assembly 100 via conduit 19. Concurrently with removal of the container 31 is the disconnection of conduit 18 from the drive unit 40, or from the pump 100. In alternative variations of the embodiment, the waste container 31 may be attached to the housing 41, or alternatively unattached thereto, and in any case positioned at any point between the pump head 44 and the housing 41.

The wound enclosure 12 comprises a vent arrangement 9, that is configured for allowing a certain degree of venting of the enclosure 12 by ambient air, when the pump assembly 100 is in operation, such as to enable a predetermined vacuum level to be maintained at the wound enclosure 12, concurrent with providing a predetermined throughflow of ambient air into the wound enclosure 12 via the venting arrangement. The venting arrangement 9 may comprise, for example, at least one bleed orifice provided at the enclosure 12, allowing ambient air to flow into and through the pumping chamber 29 via the enclosure 12, rendering enclosure 12 non-air tight, or vented.

The vent feature of this embodiment provides for introduction of air at ambient pressure to the wound area of the body 34, and thus equalization of the air pressure at the wound area with ambient pressure, whenever the vacuum pump stops pumping, allowing cyclic negative pressure application to the wound, by cycling the vacuum pump on and off alternately.

In alternative variations of the first embodiment, the vent feature 9 may be omitted.

Alternatively of or additionally to the venting arrangement 9 in the enclosure 12, a calibrated orifice or other flow restrictors may be used to provide for controlled flow of ambient air into the enclosure or into the outlet. For instance, the wound enclosure may comprise a hole plugged with open cell foam or an open pore sintered metal plug, which restrict the flow, but are not susceptible to plugging, as small dust particles will generally not plug a porous material, unlike a small orifice.

Optionally, and additionally to or instead of the vent arrangement 9, one or more ports 17 may be provided at the enclosure 12 for one or more functions. For example, one port 17 may be provided for enabling the pressure thereat to be monitored directly, for example by connecting thereto a suitable pressure transducer.

Optionally, a port 17 may be provided for connection to an irrigation source for selectively providing an irrigation fluid to the target volume.

Optionally, a controllable pressure venting arrangement may be connected to a port 17 for selectively limiting the vacuum in the wound area to a predetermined value. For example, controllable pressure venting arrangement may comprise a passive pressure regulator 35 which may be set to allow ingress of ambient air into the enclosure automatically when the vacuum level exceeds a preset maximum, thus maintaining the level of vacuum at or below this maximum. Alternatively, the controllable pressure venting arrangement may comprise an active pressure regulator, for example a solenoid coupled to a valve that serves to selectively vent the enclosure to the atmosphere when desired. Optionally, the controllable pressure venting arrangement may also comprise a biological or other suitable filter to prevent possible contamination of the wound via the confined volume V, and/or possible contamination of the external environment.

Optionally additionally or alternatively, a controllable pressure venting arrangement may be connected to be in fluid communication with control volume T for selectively limiting the vacuum in the control volume T to a predetermined value, optionally located proximal to the transducer 16. For example, controllable pressure venting arrangement may comprise a passive pressure regulator which may be set to allow ingress of ambient air into the control volume T automatically when the vacuum level exceeds a preset maximum, thus maintaining the level of vacuum at or below this maximum in the control volume T, which in turn controls the vacuum level at the enclosure 12. Alternatively, the controllable pressure venting arrangement may comprise a solenoid coupled to a valve that serves to selectively vent the control volume T to the atmosphere when desired. Particularly in variations of the first embodiment in which there is no controlled leakage outlet, such as gap 27, such a controllable pressure venting arrangement may be used for synchronizing pump head 44 with the primary pump 49.

In the first embodiment and/or alternative variations thereof, the suction head assembly 100 is joined to said waste container 31 and optionally also to conduit 18, such as to form a suction head/container unit 90. However, the suction head assembly 100 or parts thereof may be formed integrally with the waste container 31, or alternatively the components may be formed separately and joined together in any suitable manner, for example bonding, welding, fastening, and so on, to form the unit 90.

The unit 90 may be provided as a kit, which may also optionally comprise a controllable pressure venting arrangement, optionally already connected to the unit 90. Alternatively the conduit 18, container 31 and controllable pressure venting arrangement, may be provided separately. The kit may also comprises a sterile bag or other packaging (not shown) that is removed before use, and after a single or one-time use the kit is disposed of, typically in a contamination-controlled manner. Thus, the unit 90 may be made from relatively inexpensive materials, relative to, for example, the manufacturing costs of the drive unit 40, and in any case may also be made from medically compatible materials, including suitable plastics and so on.

Thus, according to one aspect of the invention, the system comprises a disposable part, including unit 90 or any components thereof, and optionally regulator 35, and a reusable part, including the pump drive unit 40.

The system 10 may be operated as follows. Unit 90 is connected to the drive unit 40 by mounting the free end of conduit 18 to a nipple 28 comprised on a port leading to pump chamber 23. In alternative embodiments, conduit 18 may be configured as part of the drive unit 40 and thus the unit 90 is connected to conduit 18 via port 58. The enclosure 12 is placed over the wound site so as to cover the same, and the periphery 51 sealingly abutting the body 34, for example with the aid of bandages, dressings, adhesive tape, and so on. The drive unit 40 is switched on, and as the motor 39 is operated, the crank turns, reciprocating the piston 22, thus causing the barrier member 15 to reciprocate by virtue of its pneumatic coupling with piston 22 via the control volume T of air, and thus alternately increases and decreases the slave pump volume P. Thus, as the suction head assembly 100 begins to operate, air and possibly fluids exuded from the wound are sucked out of the contained volume V, providing a negative pressure thereat and creating a partial vacuum. Fluids and other exudate materials in the wound are drawn and carried through the chamber 29, and out of the outlet port 14 to the container volume C via conduit 19 under positive pressure. As barrier member 15 reciprocates, it may induce partial cyclic flow within the enclosure 12, as the inlet 13 is open directly to volume V, and this may cause the pressure in the enclosure 12, and thus the pressure to the wound area on the body 34 to pulsate accordingly, i.e., to fluctuate to some degree, enhancing drainage of exudates from the wound and/or enhancing the healing process by massaging this area. As exudates fills the collection volume C, air is displaced out of this volume via vent 17. If conduit 19 becomes obstructed, there is more resistance to the barrier member 15 being pushed towards the first part 56 during a pressure stroke of the piston 22, which in turn creates a back pressure monitored by the transducer 16. The control system 300 may be programmed to counter this by increasing the action of suction head assembly 100 to increase the output pressure provided to conduit 19, for example by increasing the speed of motor 39 at pressure mode, until the obstruction is dislodged and displaced to the waste container. At the same time the suction pressure may be kept constant at a predetermined value, so that the speed of the motor 39 at suction mode is unchanged. This monitoring also allows leaks to be detected in the system, as obtaining the target vacuum level will require faster reciprocation of the piston 22.

If the container volume C of container 31 reaches full capacity, for example the collected materials or exudates reaching a maximum level, the unit 90 may be disconnected from the powered drive apparatus 40 and disposed of, in a similar manner to an end of treatment scenario, as described below, and a new unit 90 used with the powered drive apparatus 40 to continue treatment, replacing the previously used unit 90, the pump unit having been switched off while the switching of disposable components is taking place. Alternatively, it is possible to remove and dispose of the container 31 only, and to replace just this item to continue treatment. In such a case, patient discomfort is reduced, as the wound site is not disturbed. In other situations it may be necessary to change or replace the suction head assembly 100 while leaving the conduit 18 and/or the container 31 in place. According to aspects of the invention, sometimes a kit comprising the range of items suction head assembly 100, conduit 18, and container 31 is useful, while at other times a variety of kits comprising just suction head assembly 100 and conduit 18, or suction head assembly 100 and container 31, or conduit 18 and container 31, or conduit 18 or container 31 or suction head assembly 100 may also be useful.

After the completion of the suction treatment, the powered drive apparatus 40 may be switched off, and the unit 90 is disconnected from the powered drive apparatus 40, automatically pneumatically disengaging the barrier member 15 from the piston 22, and the suction head assembly 100 comprising the wound enclosure 12 is removed from the patient. The unit 90 may then be disposed of.

Thus, once set, the system 10 effectively provides a desired vacuum level at the target area TV, which is juxtaposed with the suction head assembly 100, and these conditions may be substantially maintained by indirectly monitoring the vacuum level at the wound enclosure 12 via transducer 16 and adjusting the vacuum generated by the drive unit 40 to compensate for changes thereof via a closed loop type control system, for example via system 300. The waste matter from the wound enclosure is thus suctioned to the container in a monitored and controlled manner, without contaminating the drive unit, which is regarded as a non-disposable part of the system 10. A new disposable portion, comprising a kit 90, may be immediately coupled to the powered drive apparatus 40, for immediate re-use of the system 10.

In other variations of the first embodiment of the invention, the system 10 or kit 90 may be provided without the waste container 31, mutatis mutandis, and thus the fluids drained from the system 10, rather than being collected into container 31 may be allowed to drain onto the floor, for example in an emergency, or onto a porous material, or straight into the drain, and so on.

Figure 3:
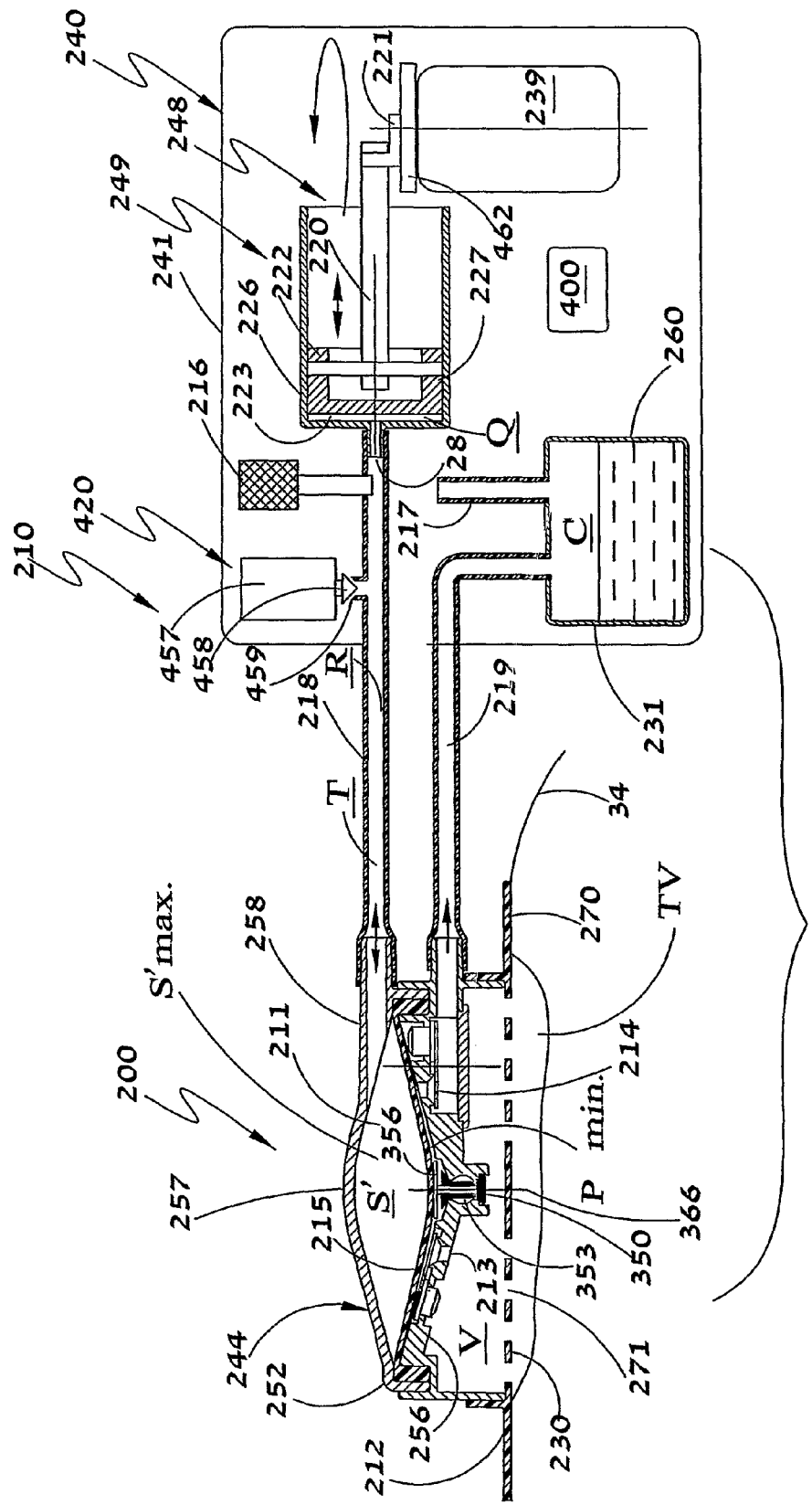
FIG. 3 is a schematic illustration in cross-sectional side view of a second embodiment of the invention, with the slave pump head in the pressure stroke.
Figure 4:
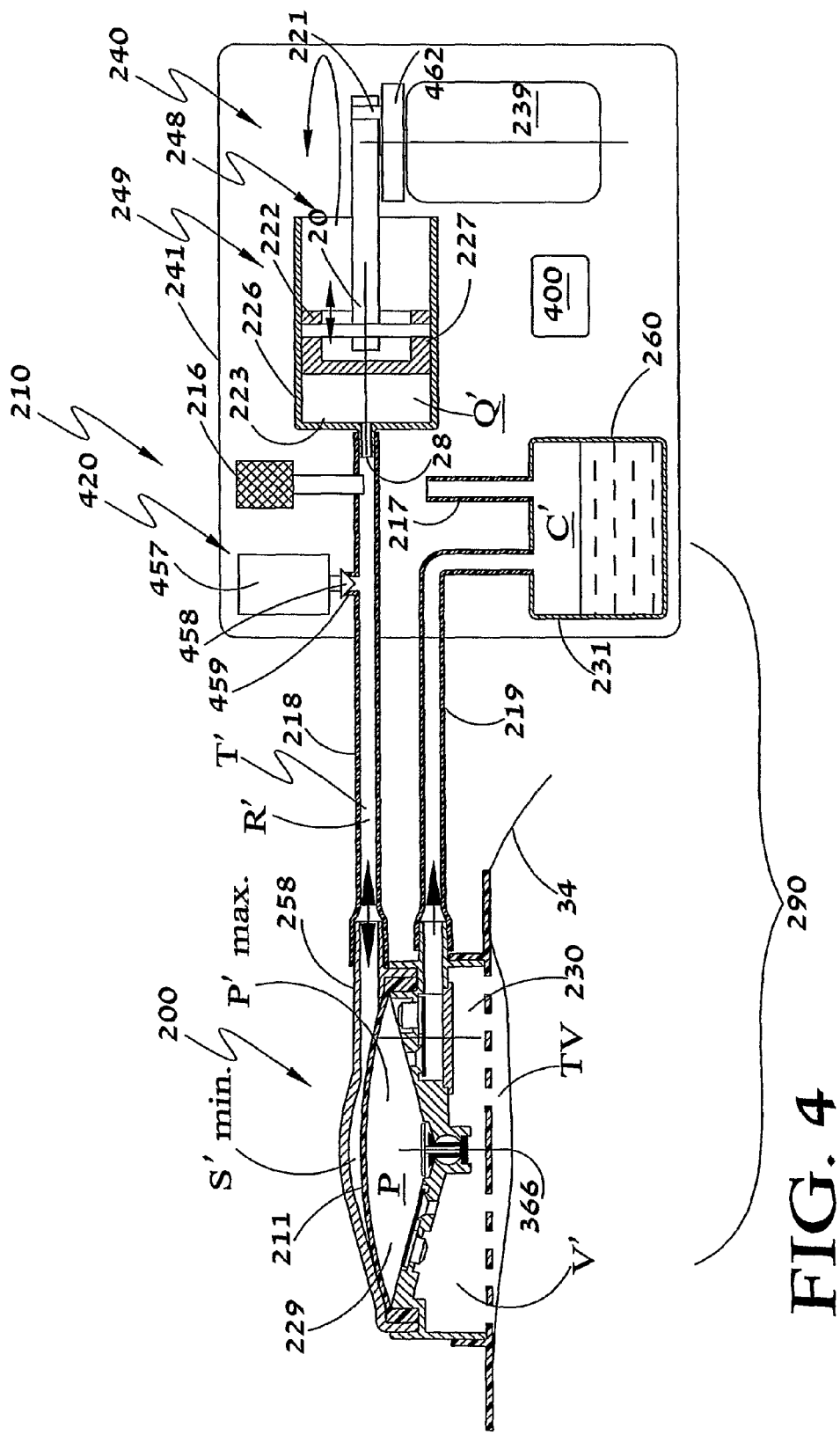
FIG. 4 shows the embodiment of FIG. 3, with the slave pump head in the suction stroke.
Figure 5:
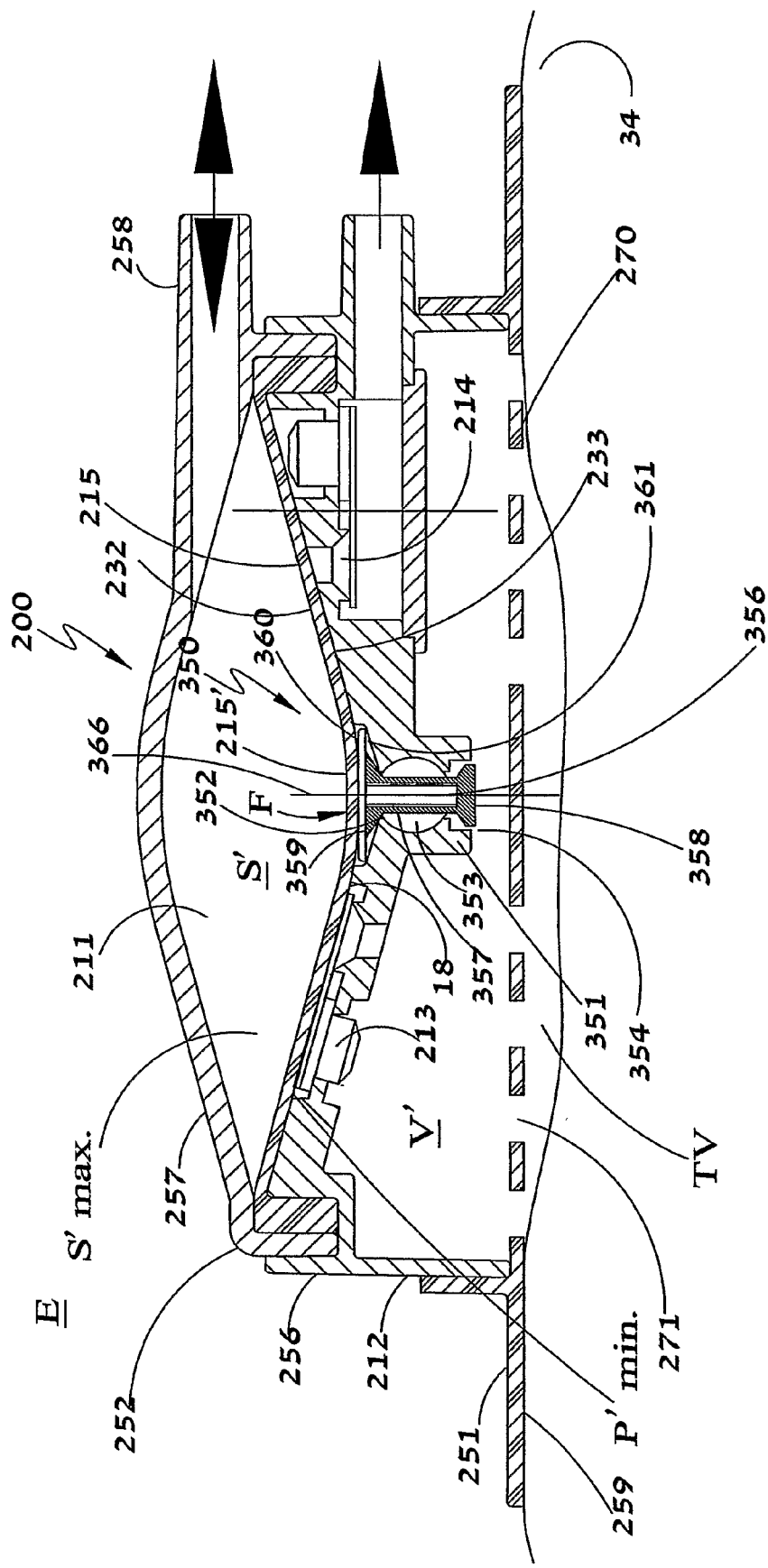
FIG. 5 shows in greater detail the suction head assembly of the embodiment of FIG. 3, with the slave pump head in the pressure stroke.

The system according to a second embodiment of the invention, is illustrated in FIGS. 3 to 5, and generally designated with the reference numeral 210, and comprises at least some elements and features that are similar to corresponding elements and features of the first embodiment, mutatis mutandis, with certain differences with respect thereto, as will become clearer herein.

The system 210 thus comprises a suction head assembly 200, waste container 231, and powered drive apparatus 240.

The suction head assembly 200 is similar to the suction head assembly as disclosed for the first embodiment or variations thereof, mutatis mutandis, but with some differences as will become clearer herein. As with the first embodiment, mutatis mutandis, the suction head assembly 200 comprises: a slave pump head 244 integrated with an enclosure in the form of wound enclosure 212 having an open end 230; the slave pump head 244 being in the form of a dual chambered diaphragm type pump head, having a substantially rigid or semi rigid casing 252 comprising a first part 256 (comprising a valved pump inlet port 213 and a valved pump outlet port 214, each provided with suitable one-way valves) and a second part 257, and a barrier member 215 (sealingly connected at its periphery to the wall of casing 252, and comprising a pump chamber facing surface 233 and an actuation chamber facing surface 232) essentially dividing the working volume of the casing 252 into a pumping chamber 229 and a juxtaposed actuation chamber 211, similar to the corresponding components as disclosed for the first embodiment, mutatis mutandis. As with the first embodiment, the arrangement is such as to ensure fluid flow in one direction through the pump head 244 from inlet port 213 to outlet port 214 via pumping chamber 229.

As with the first embodiment, mutatis mutandis, in operation, the enclosure 212 defines a confined volume V' including the target area or volume TV, in particular a medical target volume, and covers the exposed parts of the wound from which it is desired to remove under suction fluids, for example liquids and other flowable materials, which may include biological and/or non-biological materials, though at times it may be desired merely to maintain a negative pressure in the confined volume V' over the wound to promote healing thereof, for example. Furthermore, the volume V' may optionally provide unhindered passage of fluids to the pump head 244 from the target. Optionally, the volume V' may comprise any suitable interface that it may be desired to have in contact or in fluid communication with the target, so that fluid communication between the target and the pump head 244 is via the interface. Such an interface may comprise, for example, a porous and/or medicated dressing, a filter, a matrix of suitable material, porous foamed pad, gauze, and so on, and there are many examples in the art of such interfaces used in combination with a wound enclosure.

Referring in particular to FIG. 5, while the enclosure 212 according to the second embodiment does not comprise a bleed hole or passive pressure regulator, for example as comprised in the first embodiment or some variations thereof, the enclosure 212 comprises a vent valve 350 for selectively allowing and preventing fluid communication between the target volume TV and the outside environment E by enabling selectively venting therebetween. Valve 350 is generally centrally located on the first part 256, and comprises a valve housing 351, which may be integrally formed with or otherwise joined to the first part 256, having a valve outlet 354 to volume V' and defining a valve seat, and a valve inlet 353 in fluid communication with an outside of the suction head assembly 200 (and thus with respect to the external environment E) via a lumen, conduit or other suitable passageway (not shown). The valve 350 further comprises an actuable valve member 356 cooperating with said housing 351, comprising an elongate valve stem 357 and an enlarged portion 358 at one longitudinal end thereof that is configured for sealingly abutting against the valve outlet 354 when the valve 350 is in the closed position. The second longitudinal end of the valve stem 357 also comprises a second enlarged portion 359. The vent valve 350 further comprises an actuator in the form of a paddle 360 having a bar that projects into, and is accommodated in, a well formed in the valve stem 357. The bar is axially longer than the well, and thus in the non-operational, i.e. datum position of the valve 350 (FIG. 3), the paddle 360 is axially spaced from the second enlarged portion 359. The second enlarged portion 359 and the paddle 360 project from the valve housing 351 via opening 352 to said pumping chamber 229, which opening 352 is aligned with valve outlet 354 along valve axis 366. The second enlarged portion 359 and paddle 360 are accommodated in a recess 361, provided in the first part 256 and facing the barrier member 215. The valve stem 357 is made from a resilient material, such as for example rubber, and is placed in position within the valve housing 351 in a pre-tensioned state, so that enlarged portion 358 is in sealing abutment with respect to valve outlet 354 biasing the valve 350 in the closed position, with the second enlarged portion 359 is sealingly abutting against opening 352. During operation of the system 210, sealing is constantly maintained between the second enlarged portion 359 and opening 352, and in any case fluid communication between the pumping chamber 229 and the valve inlet 353 is prevented.

The pump head 244 is configured for enabling pumping of fluids therethrough (referred to herein as pumping mode of the second embodiment), and as with the first embodiment, mutatis mutandis, the barrier member 215 is also substantially impervious to the fluids being transported through the pump head 244 during operation thereof, and acts as a pumping member. The pumping chamber 229 provides a variable pumping volume P', the barrier member 215 being reversibly deformable and/or movable to provide any desired position between: a first position in general contact or close proximity to the rigid part 256, herein referred to as the full positive pressure position, to define a nominal minimum pump volume $P'_{min}$ (illustrated in FIGS. 3, 5); and a second position (when maximally spaced from the rigid part 256 during operation of the system), herein referred to as the full suction position, to define a maximum pump volume $P_{max}$ (illustrated in FIG. 4). At the same time, the actuation chamber 211 comprises a variable volume S' that varies in inverse relationship with respect to pumping volume P', so that as S' reaches a maximum value $S'_{max}$, P' reaches $P'_{min}$, and vice versa, i.e., as S' reaches a minimum value $S'_{min}$, P' reaches $P'_{max}$. Also as with the first embodiment, mutatis mutandis, barrier member 215 provides the function of isolating the pumping chamber 229 from the actuation chamber 211, such as to prevent any fluid communication or contamination therebetween, and is also configured for responding to changes in pressure between the pump chamber facing surface 233 and the actuation chamber facing surface 232 thereof such as to equalize the pressures acting on the surfaces 232 and 233 of the barrier member 215, and this condition is satisfied until the nominal minimum pump volume $P'_{min}$ is attained.

While in the second embodiment, the barrier member 215 is similar in form and structure to that of the barrier member of the first embodiment, mutatis mutandis, and in pumping mode of the pump head 244 also attempts to equalize the pressures acting on either surfaces 232 and 233 of the barrier member 215, i.e., between the two chambers 211, 229, by changing the relative magnitudes of the volumes thereof, the barrier member 215 in the second embodiment is used, in an operational mode of the system 210 referred to herein as vent mode of the second embodiment, also for mechanically actuating the valve 350. Thus, the pump head 244 is further configured to controllably vent the enclosure 212 by further operation of the bather member 215 in vent mode. In the aforesaid vent mode, the pump head 244 is configured to enable at least a part 215' of the barrier member 215 to be displaced and/or translated and/or deformed beyond that required for providing the nominal minimum pump volume $P'_{min}$ so as to apply a mechanical force to the valve stem 357 via the paddle 360. Thus, in vent mode, the barrier member 215 subjected to an additional pressure differential beyond that required to provide the nominal minimum pump volume $P'_{min}$, and part 215' of the barrier member 215 abuts and applies the aforesaid mechanical force to paddle 251, such as to axially displace the valve stem 357 in a direction away from the barrier member 215, first increasing the tension of the valve stem 357 as the bar stretches the valve stem, and eventually unseating the enlarged portion 358 from the outlet 354 as the paddle approaches and optionally abuts the second enlarged portion, so as to open the valve 350, allowing fluid communication between the target volume TV and the external environment E. The opening of the valve 350 thus occurs at a nominally constant minimum pump chamber volume, $P'_{min}$, and while no actual pumping is taking place. During regular pumping mode of said system 210, when the valve 350 is in the closed position, the target area TV and volume V' are substantially sealed from the external environment.

In at least some variations of this embodiment, other suitable arrangements may be provided for the vent valve that enable the same to selectively vent enclosure 212 when the vent valve is mechanically acted upon by the barrier member 215 at the end of the pressure stroke.

In yet other alternative variations of the second embodiment, the valve 350, including the associated passage to the outside of the suction head assembly 200, may be omitted from the suction head assembly 200.

In the second embodiment, the enclosure 212 has a flexible outer rim or flange 251 that is sealable to the periphery of the wound area on the body 34. The flange 251 may be made of a compliant material, such as for example polyurethane, which facilitates conforming of the flange 251 to the perimeter of the body part surrounding the target wound area TV. Optionally, the lower rim 259 of the flange may comprise an adhesive coating, which prior to use may be covered with a suitable removable tape for example, for facilitating application and sealing of the rim to the target area or volume, i.e., the wound area. Furthermore, the enclosure 212 comprises a screen 270 at or near the open end 230, the screen 270 having a plurality of openings 271 configured for allowing adequate fluid communication between the target area and the enclosure 212, while preventing solid matter such as large particles that may be present at the target area from being suctioned by the system 210 during operation thereof, and thus minimize the risk of the valves and/or pumping chamber 229 becoming clogged with such matter. In the second embodiment, the flange 251 and screen 270 are in the form of a unitary body, which is adapted for being mounted to the enclosure 212 by any suitable means, for example, heat welding, bonding, and so on.

Alternatively, and in other variations of this embodiment, the flange 251 and screen 270 may be joined to one another, and further optionally may be joined to, or may be integral with, the enclosure 212. In yet other variations of this embodiment, the enclosure 212 may dispense with one or both of the flange 251 and screen 270, and is in any case adapted for being sealingly attached to the periphery of the desired target area on the body 34 in a different manner, for example as disclosed for the first embodiment, mutatis mutandis.

While the flange 251 and screen 270 have been described in the context of the second embodiment, the enclosure 12 according to a variation of the first embodiment may also be similarly fitted with one or both of a flange and screen, similar to the flange 251 and screen 270 of the second embodiment, mutatis mutandis.

Optionally, one or more ports (not shown) may be provided at the enclosure 212 for one or more functions. For example, one such port may be provided for enabling the pressure thereat to be monitored directly, for example by connecting thereto a suitable pressure transducer. Optionally, another such port may be provided for connection to an irrigation source for selectively providing an irrigation fluid to the target volume.

System 210 also comprises conduit 219 and waste container 231 (comprising housing 260 defining a collection volume C', and vent 217), substantially similar to conduit 19 and waste container 231 as disclosed for the first embodiment or variations thereof, mutatis mutandis, and conduit 219 similarly provides fluid communication between the pump volume P' and the container 231 via outlet port 214. As with the first embodiment or variations thereof, the said waste container 231 may be accommodated in or attached to housing 241, or may be positioned anywhere between the pump head 244 and the powered drive apparatus 240, and may be selectively removed therefrom for disposal, for example, optionally while still connected to the suction head assembly 200 via conduit 219. Concurrently with removal of the container 231 is the disconnection of conduit 218 from the powered drive apparatus 240, or from the suction head assembly 200.

The powered pump, apparatus 240 comprises drive unit 239 and primary pump 249. The drive unit 239 is accommodated in housing 241, and comprises a powered drive in the form of electric motor 239, and an optional battery pack (not shown) for powering the motor. Additionally or alternatively, the motor 239 may be provided with power from an external source, such as for example an electric mains (not shown). A reciprocating mechanism 248, comprising a crank 221 coupled to a reciprocating rod 220, is provided within the housing 241 for converting the rotary drive of the motor 239 to reciprocating motion of rod 220. The powered drive apparatus 240 is coupled to primary pump 249, which in this embodiment is in the form of a piston pump, comprising a piston 222 reciprocable within a cylinder 226 to provide a master pump chamber 223 having a variable pumping volume Q'. The reciprocating rod 220 is connected to the piston 222, which is driven in a two-way forced reciprocation manner by means of the rod when the system 210 is in operation to enable the magnitude of volume Q' to be varied within a desired range bounded by a desired maximum value $Q'_{max}$ and a minimum value $Q'_{min}$ corresponding to the suction stroke limit (bottom dead center, or BDC) and to the pressure stroke limit (top dead center, or TDC), respectively.

The pump head 244, in particular the second part 257, comprises a port 258 that provides fluid communication between the actuation chamber 211 and the powered drive apparatus 240, in particular the master pump chamber 223, via a conduit 218 or the like having internal volume R'. The pumping volume Q', volume S' and the internal volume R' together define a control volume of working fluid that couples the piston 222 with the barrier member 215. In the second embodiment, the working fluid is preferably air, and thus the control volume T' pneumatically couples the master pump chamber 223 with the actuation chamber 211, though in variations of this embodiment different fluids may be used for the pneumatic coupling.

In the second embodiment, the maximum change in volume Q', i.e., in displacement ΔQ', of the master pump chamber 223 between $Q'^{max}$ and $Q'_{min}$, i.e., $\Delta Q'_{max}$ is substantially larger than the maximum capacity or volume $S'_{max}$ of the actuation chamber 211. Furthermore, the piston 222 has a full positive pressure position (corresponding to the full positive pressure position of the barrier member 215) though this is short of TDC. Similarly, the piston 222 has a full suction position (corresponding to the full suction position of the barrier member 215) and this may be short of BDC or alternatively at BDC. The actual full positive pressure position and the actual full suction position of the piston 222 within the cylinder 226 may vary according to the pneumatic pressure of volume T', which in operation of the system 210 may be variable.

The system 210 further comprises at least one pressure sensor or transducer 216 or any other suitable air pressure measuring device in fluid communication with control volume T', for monitoring the pressure therein. In the illustrated embodiment, the transducer 216 comprises a conduit spliced into conduit 218, and is furthermore operatively connected to control system 400. The control system 400 may thus be adapted for monitoring and optionally controlling at least one operative parameter of the motor 239. The transducer 216 provides feedback signals or data—for example electrical, electronic or digital—thereto representative of the absolute or gauge pressure in the actuation chamber 211, and thus of the pressure in pump chamber 229.

The suction pressure that can be induced at the pump chamber 229 in pump mode is nominally equal to that at the wound enclosure 212, since the two are juxtaposed and in close proximity in terms of fluid communication, via port 213, as described for the first embodiment, mutatis mutandis. Thus, the peak suction pressure at the chamber 223 nominally closely corresponds to the peak suction pressure provided at the wound enclosure 212, and thus monitoring of the chamber pressure via transducer 216 generally provides a measure of the pressure at the enclosure 212; at the same time, the transducer 216 is effectively isolated from the pump chamber 229 via the barrier member 215. In other variations of the second embodiment of the invention, the piston pump arrangement for the primary pump 249 may be replaced with a diaphragm type pump arrangement, for example, in which the pump volume Q' is instead defined by a chamber formed between a diaphragm and a casing of the pump arrangement, the diaphragm being coupled to the motor to reciprocate as the motor turns. Operation of this arrangement is otherwise identical to that of the piston pump arrangement described above for the second embodiment, mutatis mutandis.

The drive unit 239 is a stepper motor, which enables the rotation thereof to be selectively reversed so that the motor can reverse its operating direction without having to complete a full turn, driving the piston to translate to any variable desired stroke and applying a correspondingly variable pressure or vacuum to volume T', as desired. The rotation of the motor 239, clockwise (CW) or counter-clockwise (CCW), may be accurately controlled in a stepwise manner, enabling any desired CW or CCW angular displacement of the crank 221 to be provided, and at any desired angular speed, within the operating range of the motor 239, and enables the vacuum/pressure levels induced at the enclosure 212 to be controlled accurately. Control system 400 is further configured for controlling operation of the motor 239, including angular displacement, angular speed, angular acceleration, direction of turning and so on. Controllable stepper motors and programmable control units for controlling the rotation of the same in very precise and predetermined ways, are well known and commonly used, and do not require further description herein.

In one mode of operation when in pump mode, the piston 222 is reciprocated at a displacement less than the full stroke, and the motor 239 is operated to turn the crank 221 in one direction, say CW, from a suitable datum position for a predetermined angular displacement, and then reverses this displacement by turning the crank 221 in the opposite angular direction, in this case CCW. This controlled oscillating motion of the crank 221 provided by the motor 239 drives reciprocation of the piston 222, applying a cyclic pressure and setting up a corresponding pulsating flow in the control volume T', alternately increasing and decreasing the volume of the actuation chamber 211, which in turn respectively decreases and increases the volume P' of slave pump chamber 229, pneumatically causing a corresponding displacement and/or deformation of the barrier member 215, which in turn causes the volume of pump chamber 229 to contract and expand, providing a periodic suction force in the enclosure 212. Thus, fluids in the enclosure 212 may be periodically sucked directly into pump chamber 229 via inlet 213, and then out of the pump chamber 229, under pressure, to the container 231 via outlet 214 and conduit 219.

In this mode, the pressure within the chamber 223 thus fluctuates in a cyclic manner, and the peak suction pressure in the chamber 223, which corresponds to the maximum travel of the piston in one direction corresponding to the aforesaid angular displacement of the crank in one direction (e.g. CW), provides a nominally equal peak suction level at the pump chamber 229, since the barrier member 215 is actuated by deforming and/or translating to equalize pressure across it. Similarly, the peak positive pressure in the chamber 223, which corresponds to the maximum travel of the piston in the other direction corresponding to the aforesaid reverse angular displacement of the crank in the other direction (respectively CCW), provides a nominally equal peak positive suction level at the pump chamber 229, since the barrier member 215 is actuated in the opposite direction to equalize pressure across it.

The actual angular displacement of the crank 221 can be set at any desired value up to a first threshold value, which corresponds to providing a displacement ΔQ', i.e., change in volume between peak suction and peak pressure in the chamber 223 that is substantially equal to the maximum displacement volume of the actuation chamber 211, and the suction and positive pressure generated by the pumping chamber 229 will be set at a corresponding value up to a maximum value, at which the volume of the pumping chamber 229 is alternated between $P_{max}$ and $P_{min}$. Thus, at the first threshold value, the piston 222 is reciprocated between the said full suction position and said full positive pressure position thereof.

If the motor 239 is operated to provide oscillatory angular displacements for the crank 221 beyond the first threshold value but up to a second, higher, threshold value, the pump chamber 223 will effectively attempt to alternately push and suck a larger volume than the volumetric capacity of actuating chamber 211, but this will have no effect on the pumping capacity of the pump chamber 229, which will continue to operate at nominally maximum capacity, its volume alternating between $P_{max}$ and $P_{min}$. However, the greater the magnitude of the aforesaid angular displacement past the first threshold, the greater the actual gauge pressure acting on the barrier member 215, which, when the pumping chamber 229 is at $P_{min}$, abuts onto and applies a corresponding force on the valve 350. At the aforesaid second threshold value, the gauge pressure is such that the force F applied to the valve 350 by the barrier member 215 is sufficient for opening the valve 350, thus invoking the vent mode and ventilating the enclosure 212 effectively at the end of the pressure stroke of the pump chamber 229. Of course, as soon as the crank 221 thereafter changes angular direction, the actuation force on the valve 350 by the barrier member 215 ceases, interrupting venting of the enclosure 212; the enclosure is again sealed with respect to the external environment, and application of a suctioning force in volume V continues.

The second threshold corresponds to an angular displacement of the crank 221 of half a turn (180°) or less.

The vent valve feature of this embodiment provides for selective introduction of air at ambient pressure to the wound area of the body 34, and thus equalization of the air pressure at the wound area with ambient pressure, whenever the primary pump is in the pressure stroke and creating a pressure in volume T' higher than is required for the purging of exudates and fluids from pump chamber 229, allowing cyclic negative pressure application to the wound, by cycling the vacuum alternately between pimp mode and vent mode.

Alternatively, the motor 239 may be operated to provide full rotational motion in one angular direction, and this periodically reciprocates the piston fully between TDC and BDC, providing maximum pumping by the pump chamber 229, the pressure part of each pumping cycle being followed by venting prior to the next pumping cycle.

The control system 400 controls the operation of the motor 239 to provide the required angular displacements, which can be provided in small incremental steps, for example angular steps of 1.8°, as well as change in angular direction of the crank 221, and also allows the crank 221 to be stopped and parked in any desired angular position. In one mode of operation, the motor 239 is controlled so that the angular speed and acceleration induced on the crank 221 is substantially the same in each of the two directions, CW and CCW. In a different mode of operation, the motor 239 may be controlled so that the angular speed and/or acceleration induced on the crank 221 is different along each of the two opposite directions CW and CCW during each oscillation cycle. In other words, the speed and/or acceleration of the crank 221 may be constant or varied, as desired, up to the first or second thresholds along one angular direction, and the speed and/or acceleration of the crank 221 may be constant or varied, as desired, along the opposed direction, in the same or in a different manner.

For example, the motor 239 can be controlled by control system 400 to slow its rotational speed at angular positions of the crank 221 which correspond to the opening of one or another of the valves 213 or 214, and the speed is raised after the respective valve is fully open. This feature can provide noise reduction benefits.

The motor 239 can also be controlled by control system 400 to provide a predetermined suction level in the enclosure 212. For example, the crank 221 may be driven by the motor 239 through one or more pumping cycles (in pump mode only) until the appropriate suction pressure is obtained at the enclosure 212, which may be at an intermediate point within a suction part of the cycle, whereupon the motor 239 is stopped and the crank parked in the corresponding position, thereby maintaining the pressure until the motor is activated further. The actual suction pressure may be monitored via transducer 216, and a closed loop control may be provided by controller 400 for operation of the motor 239 based on feedback provided by the transducer 216. Since the enclosure 212 is effectively sealed onto the body part, the vacuum level is maintained. Of course, any unwanted leaks can be compensated for by continuing to operate the motor in the aforesaid closed loop control manner as required.

As illustrated in FIGS. 3 and 4, the motor 239 further comprises a flywheel 462, which is connected to or is integral with the crank 221. The flywheel 462 is configured for dampening vibration of the motor and crank, particularly as the stepper motor 239 incrementally "steps" to provide the desired rotation thereof. A feature of operation of the system 210 with the flywheel 462 is that noise emission may be reduced. The flywheel is optional, and thus in at least some variations of the second embodiment, the flywheel may be omitted.

In alternative variations of the second embodiment, a different drive unit may be used instead of a stepper motor, for example as disclosed for the first embodiment and variations thereof, mutatis mutandis.

The system 210 further comprises a controllable venting arrangement 420 for enabling synchronization of operation between the pump head 244 and primary pump 249. Synchronization is often required after connecting the pump head 244 and primary pump 249 via conduit 218 and prior to using the system in pump mode, to ensure that the full suction position of the barrier member 215 corresponds to the full suction position of the piston 222, and similarly, that full positive pressure position of the barrier member 215 corresponds to the full pressure position of the piston 222.

Venting arrangement 420 comprises a venting valve 459, which is actuable via a solenoid 457, controllable via the controller 400 to which it is operatively connected. The valve 459 is in fluid communication with control volume T', and is located on a conduit 459 spliced into conduit 218. In the second embodiment, the control volume T' is substantially air tight, once the system 210 is operational, and after synchronization.

Synchronization may be achieved in a number of ways, and does not depend on the initial position of the barrier member 215 within the pump head 244 or of the initial position of the piston 222 within the primary pump 249.

For example, the control system 400 controls the solenoid 457 to open the valve 459, and then the motor 239 to turn the crank 221 so that the piston 222 is at its full suction position, i.e. at BDC. The valve 459 is then closed, and as the piston 222 is slowly displaced towards the TDC position, the pressure is monitored by the transducer 216. If the barrier member 215 is at its full suction position, the system 210 is already synchronized, and movement of the piston 222 to the position corresponding to the full positive pressure position of the barrier member 215 (which is known by the controller 400) will result in no increase in pressure monitored by the transducer, the barrier member 215 being moved until it has reached its full positive pressure position. On the other hand, if the barrier member 215 is at its full positive pressure position or indeed at any position other than the full suction position, movement of the piston 222 to the position corresponding to the full positive pressure position of the barrier member 215 will at some point, depending on the actual position of the barrier member 215, result in an increase in pressure monitored by the transducer. When the piston 222 has reached the position corresponding to the full positive pressure position of the barrier member 215, the increased pressure will have ensured that the barrier member 215 is at its full positive pressure position as well, and the controller 400 may momentarily open the valve 459 to allow synchronization of the position of piston 222 relative to the position of the barrier member 215.

In alternative variations of this embodiment the system 210 may be synchronized when barrier member 215 is in the full suction position, mutatis mutandis. In yet other variations of this embodiment, the venting arrangement 420 may be omitted, and the pump head 244 may be synchronized with the primary pump 249, prior to using the system 210, in a different manner, for example by manually setting the barrier member 215 to its full suction position and the piston 222 close to its full suction position and interconnecting the two via conduit 218 while not disturbing the respective positions of the barrier member 215 or the piston 222.

In the second embodiment and/or at least some variations thereof, the suction head assembly 200 is joined to said waste container 231 (and optionally in at least some variations of the second embodiment, also to conduit 218), such as to form a suction head/container unit 290. However, the suction head assembly 200 or parts thereof may be formed integrally with the waste container 231, or alternatively the components may be formed separately and joined together in any suitable manner, for example bonding, welding, fastening, and so on, to form the unit 290. As with the first embodiment and variations thereof, mutatis mutandis, the unit 290 may be provided as a kit, or alternatively the head assembly 200 and container 231 (and optionally conduit 218), may be provided separately. The kit may also comprises a sterile bag or other packaging (not shown) that is removed before use, and after a single or one-time use the kit is disposed of, typically in a contamination-free manner. Thus, the unit 290 may be made from relatively inexpensive materials, compared with, for example, the manufacturing costs of the powered drive apparatus 240, and in any case may also be made from medically compatible materials, including suitable plastics and so on.

Thus, according to one aspect of the invention, the system comprises a disposable part, including unit 290 or any components thereof, and a reusable part, including the powered drive apparatus 240.

The system 210 may be operated as follows. Unit 290 is connected to the powered drive apparatus 240 by connecting conduit 218 to port 258. The enclosure 212 is placed over the wound site so as to cover the same, and the flange 251 sealingly abutting the body 34, for example via its adhesive rim and/or with the aid of bandages, dressings, adhesive tape, and so on.

Synchronization of the pump head 244 and primary pump 249 is then carried out, as disclosed above. The control system 400 is then set to the particular mode of operation desired by the user. If it is desired to maintain a particular negative pressure at the wound site, the powered drive apparatus 240 is activated and the motor 239 is run until the pressure reaches the desired level, as monitored by transducer 216, whereupon the motor is stopped, as disclosed above. If continuous pumping is additionally or alternatively required, for example for pumping exudates from the target area or volume, i.e., the wound site, the system 210 is used in pump mode, as described above. If pumping and venting of the wound site is additionally or alternatively required, then the system 210 is used alternately in pump mode and vent mode, as disclosed above.

Fluids and other exudate materials in the wound that are drawn and carried through the chamber 229, and out of the outlet port 214 are collected in the container volume C' via conduit 219 under positive pressure, in a similar manner to that disclosed for the first embodiment, mutatis mutandis, and air is displaced out of this volume via vent 217. In some modes of operation, as barrier member 215 reciprocates, it may induce partial cyclic flow within the enclosure 212, as the inlet 213 is open directly to volume V', and this may cause the pressure in the enclosure 12, and thus the pressure to the wound area on the body 34 to pulsate accordingly, i.e., to fluctuate to some degree, enhancing drainage of exudates from the wound and/or enhancing the healing process by massaging this area.

If during operation of the system 210 conduit 219 becomes obstructed, there is more resistance to the barrier member 215 being pushed towards the first part 56 during a pressure stroke of the piston 222, which in turn creates a back pressure monitored by the transducer 216. The control system 400 may be programmed to counter this by increasing the action of suction head assembly 200 to increase the output pressure provided to conduit 219, for example by increasing the displacement of the piston 222 at each pressure stroke, until the obstruction is dislodged and displaced to the waste container. At the same time the suction pressure may be kept constant at a predetermined value by stopping rotation of the motor at a particular angular position. This monitoring also allows leaks to be detected in the system, as when operating in pump mode only, a leak results in the motor having to be run continuously for maintaining a particular vacuum level. On the other hand, when there are no leaks (and no venting), the motor only needs to turn and drive the pump as much as is required to compensate for the volume of exudates and fluids pumped from the target area.

If the container volume C' of container 231 reaches full capacity, for example the collected materials or exudates reaching a maximum level, the unit 290 may be disconnected from the powered drive apparatus 240 and disposed of, in a similar manner to an end of treatment scenario, as described below, and a new unit 290 used with the powered drive apparatus 240 to continue treatment, replacing the previously used unit 290, the pump unit having been switched off while the switching of disposable components is taking place. Alternatively, it is possible to remove and dispose of the container 231 only, and to replace just this item to continue treatment. In such a case, patient discomfort is reduced, as the wound site is not disturbed. In other situations it may be necessary to change or replace the suction head assembly 200 while leaving the container 231 in place. According to aspects of the invention, sometimes a kit comprising the range of items suction head assembly 200 and container 231 is useful, while at other times a variety of kits comprising just suction head assembly 200 or container 31, may also be useful.

After the completion of the suction treatment, the powered drive apparatus 240 may be switched off, and the unit 290 is disconnected from the powered drive apparatus 240, automatically pneumatically disengaging the barrier member 215 from the piston 222, and the suction head assembly 200 comprising the wound enclosure 212 is removed from the patient. The unit 290 may then be disposed of. A new disposable portion, comprising a new unused kit 290, may be immediately coupled to the powered drive apparatus 240, for immediate re-use of the system 210.

In variations of the second embodiment of the invention, the system 210 or kit 290 may be provided without the waste container 231, mutatis mutandis, and thus the fluids drained from the system 210, rather than being collected into container 231 may be allowed to drain onto the floor, for example in an emergency, or onto a porous material, or straight into the drain, and so on.

It is clear that the present invention alleviates the need for cleaning or disinfecting any portion of drive unit after use, or providing protective means, such as filters, to keep contaminants from reaching the costly drive.

While the invention, according to the first and second embodiments, and variations thereof, has been described in the context of a medical target volume comprising a wound, burn or the like, the target volume may, in other applications of the invention, comprise instead a system, environment, and so on, which for example may be contaminated with chemical and/or biological and/or other contaminants, regarding which it is beneficial to remove contaminated fluids therefrom, or indeed in other embodiments any system, environment, and so on, in which it is desired to remove fluids therefrom.

It should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A system for providing suction to a target area, comprising: a suction head assembly comprising an enclosure configured for covering the target area such that the target area is enclosed in the enclosure and in fluid communication therewith, the enclosure having an open end adapted to be in fluid communication with at least a portion of the target area via the open end, and a pump head comprising a pumping chamber having an inlet and an outlet, the pump head being integrated with the enclosure, and wherein the inlet is comprised in the enclosure and is in fluid communication therewith; a powered drive apparatus comprising a drive unit coupled to a primary pump, and a non-mechanical coupling arrangement for connecting the primary pump to the pump head, in operation the powered drive apparatus being configured for operating the pump head via the non-mechanical coupling arrangement when driven by the drive unit; wherein the system is adapted for selectively providing a predetermined working pressure within the enclosure below ambient pressure of an external environment via operation of the pump head, wherein the pump head comprises an actuation chamber that is mechanically coupled to the pumping chamber, and wherein the non-mechanical coupling arrangement comprises a pneumatic or hydraulic coupling arrangement comprising a control volume of working fluid that respectively pneumatically or hydraulically couples the primary pump with the actuating chamber, the mechanical coupling being configured for enabling the drive unit to operate the pump head by inducing pumping of the pumping chamber via pneumatic coupling or hydraulic coupling, respectively, between the primary pump and the actuation chamber.

2. The system according to claim 1, wherein the pump head and the enclosure are integrally joined with or mounted to one another.

3. The system according to claim 2, wherein the enclosure comprises at least one flange made from a compliant material and sealable over a body part comprising the target area and a screen provided at the open end.

4. The system according to claim 2, wherein the suction head assembly is remotely releasably connected to the powered drive apparatus via the non-mechanical coupling arrangement.

5. The system according to claim 1, wherein the powered drive apparatus is remote from the suction head assembly.

6. The system according to claim 1, wherein the mechanical coupling comprises a pump member included in the pump head and defining part of the pumping chamber and part of the actuation chamber, wherein the pump member is actuable via the pneumatic coupling or hydraulic coupling to generate the working pressure, and wherein the pump member constitutes a fluid barrier member substantially preventing fluid communication between the enclosure and the pump drive.

7. The system according to claim 6, wherein the pump head comprises a casing, and pump member is in the form of a diaphragm having first and second opposite facing surfaces and sealingly mounted at a periphery thereof to an inside of the casing to divide the inside of the casing, respectively defining the pump chamber, comprising the first surface, and the actuating chamber, comprising the second surface, and wherein the pump member is configured for offering no substantial resistance to deformation and/or movement under the action of a pressure differential across the first and second surfaces.

8. The system according to claim 1, further comprising a waste container defining a collection volume for collection of materials that may be drained from the target area via the suction head assembly driven under positive pressure from the pumping chamber towards the waste container during operation of the system, wherein the waste container is in fluid communication with the outlet of the pumping chamber, and wherein at least one of the suction head assembly and the waste container is configured for being disposable.

9. The system according to claim 1, further comprising at least one of: a non fluid invasive monitoring system, with respect to fluids to be sucked via the pump head, for monitoring the working pressure, the monitoring system comprising at least one pressure sensor in fluid communication with a control volume and configured for monitoring a pressure in the control volume; a control system for controlling operation thereof; a venting arrangement configured for providing, at least during operation of the system, substantially permanent fluid communication between the enclosure and the external environment to enable the working pressure to be maintained at the target area while enabling a desired flow rate of ambient air into the enclosure to be provided via the venting arrangement.

10. The system according to claim 1, further comprising a controllable venting arrangement configured for controlling, at least during operation of the system, the vacuum level at a control volume.

11. The system according to claim 1, the enclosure further comprising a port configured for connection to an irrigation source for providing, at least during operation of the system, fluid communication between the enclosure and the irrigation source to enable irrigation of the target area with a desired irrigation material.

12. The system according to claim 1, further comprising a first venting arrangement adapted for providing, at least during operation of the system, selective fluid communication between the enclosure and the external environment, such as to enable the target area to be selectively vented to ambient pressure via the first venting arrangement.

13. The system according to claim 12, wherein the first venting arrangement comprises a passageway between the enclosure and an outside environment and having a venting valve which is biased in its datum configuration to close fluid communication via the passageway, the venting valve being configured to be openable responsive to a predetermined force acting thereon, wherein the system is configured for selectively providing the force via the pump head, under conditions wherein the primary pump provides a pressure stroke beyond that required for actuating the pump head to provide a maximum positive pressure at the pump chamber.

14. The system according to claim 1, further comprising a controllable venting arrangement adapted for selectively regulating the pressure level of a control volume.

15. The system according to claim 14, wherein the controllable venting arrangement is configured for synchronizing the system by controlling the fluid pressure in the control volume prior to operative use of the system.

16. A system for providing suction to a target area, comprising: a suction head assembly comprising an enclosure configured for covering the target area such that the target area is enclosed in the enclosure and in fluid communication therewith, the enclosure having an open end adapted to be in fluid communication with at least a portion of the target area via the open end, and a pump head comprising a pumping chamber having an inlet and an outlet, the pump head being integrated with the enclosure, and wherein the inlet is comprised in the enclosure and is in fluid communication therewith; a powered drive apparatus comprising a drive unit coupled to a primary pump, and a non-mechanical coupling arrangement for connecting the primary pump to the pump head, in operation the powered drive apparatus being configured for operating the pump head via the non-mechanical coupling arrangement when driven by the drive unit; wherein the system is adapted for selectively providing a predetermined working pressure within the enclosure below ambient pressure of an external environment via operation of the pump head,
- wherein the pump head and the enclosure are integrally joined with or mounted to one another, and
- wherein the primary pump comprises a primary pump member adapted for forced reciprocation within a primary pump casing and the pump drive comprises a rotary motor, and wherein the powered drive apparatus comprises a reciprocation arrangement for converting rotary motion of the motor to reciprocative motion of the primary pump member, the primary pump member being in fluid communication with an actuation chamber via a control volume during operation of the system.

17. The system according to claim 16, wherein the system is configured according to at least one of: wherein the pump member comprises a piston member, and wherein the pump member and the piston member are pneumatically coupled or hydraulic coupled one with the other via the control volume at least when the system is in operation; wherein the primary pump comprises bleeding means for allowing controlled fluid communication between the control volume and an outside environment, the bleeding means being of predetermined size to allow for the relative synchronization between the primary pump member and the actuation chamber; and wherein the actuation chamber is configured for displacing a first maximum volume of working fluid within the control volume between maximum and minimum extremes of actuation of the pump member respectively corresponding to a maximum positive pressure and a maximum suction pressure induced at the pumping chamber, and wherein the primary pump is configured for displacing a second maximum volume of working fluid within the control volume as the primary pump element undergoes a reciprocation cycle, wherein the second maximum volume is greater than the first maximum volume.

18. The system according to claim 16, wherein the pump drive comprises a stepper motor.

19. The system according to claim 18, wherein the system is configured for operating the motor to selectively turn in any direction for any desired angular displacement and to selectively reverse direction.

20. The system according to claim 19, wherein the system is configured for operating the motor to be alternately turned in clockwise and counterclockwise directions through respective positive and negative angular displacement of predetermined size to provide a corresponding reciprocation of the primary pump element and generating a respectively alternating positive pressure and suction pressure at the pumping chamber to thereby generate the working pressure at the enclosure in operation of the system, wherein levels of the positive pressure and suction pressure are a function of the angular displacement up to a first maximum angular displacement corresponding to the maximum and minimum extremes of actuation of the pump member respectively, wherein in operation of the system, the enclosure is sealingly affixed over the target area.

21. A system for providing suction to a target area, comprising: a suction head assembly comprising an enclosure configured for covering the target area such that the target area is enclosed in the enclosure and in fluid communication therewith, the enclosure having an open end adapted to be in fluid communication with at least a portion of the target area via the open end, and a pump head comprising a pumping chamber having an inlet and an outlet, the pump head being integrated with the enclosure, and wherein the inlet is comprised in the enclosure and is in fluid communication therewith; a powered drive apparatus comprising a drive unit coupled to a primary pump, and a non-mechanical coupling arrangement for connecting the primary pump to the pump head, in operation the powered drive apparatus being configured for operating the pump head via the non-mechanical coupling arrangement when driven by the drive unit; wherein the system is adapted for selectively providing a predetermined working pressure within the enclosure below ambient pressure of an external environment via operation of the pump head,
- further comprising at least one of: a non fluid invasive monitoring system, with respect to fluids to be sucked via the pump head, for monitoring the working pressure, the monitoring system comprising at least one pressure sensor in fluid communication with the control volume and configured for monitoring a pressure thereof; a control system for controlling operation thereof; a venting arrangement configured for providing, at least during operation of the system, substantially permanent fluid communication between the enclosure and the external environment to enable the working pressure to be maintained at the target area while enabling a desired flow rate of ambient air into the enclosure to be provided via the venting arrangement,
- wherein the system comprises the venting arrangement, and the venting arrangement comprises at least one bleeding orifice comprising an effective flow area compatible with providing the desired flow rate, and further comprising a controllable venting arrangement configured for regulating, at least during operation of the system, the vacuum level at the target area, wherein the controllable venting arrangement comprises any one of a pressure regulator and a solenoid valve.

* * * * *